US009662490B2

(12) United States Patent
Tracey et al.

(10) Patent No.: US 9,662,490 B2
(45) Date of Patent: *May 30, 2017

(54) METHODS AND SYSTEMS FOR REDUCING INFLAMMATION BY NEUROMODULATION AND ADMINISTRATION OF AN ANTI-INFLAMMATORY DRUG

(71) Applicant: The Feinstein Institute for Medical Research, Manhasset, NY (US)

(72) Inventors: Kevin J. Tracey, Old Greenwich, CT (US); Mauricio Rosas-Ballina, Bayside, NY (US); Michael A. Faltys, Valencia, CA (US); Ralph J. Zitnik, Santa Barbara, CA (US)

(73) Assignee: The Feinstein Institute for Medical Research, Manhasset, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/967,149

(22) Filed: Dec. 11, 2015

(65) Prior Publication Data

US 2016/0096016 A1    Apr. 7, 2016

Related U.S. Application Data

(63) Continuation-in-part of application No. 12/415,671, filed on Mar. 31, 2009, now Pat. No. 9,211,409.

(60) Provisional application No. 61/072,603, filed on Mar. 31, 2008.

(51) Int. Cl.
*A61N 1/32* (2006.01)
*A61N 1/34* (2006.01)
*A61N 1/36* (2006.01)

(52) U.S. Cl.
CPC ......... *A61N 1/327* (2013.01); *A61N 1/36053* (2013.01); *A61N 1/326* (2013.01); *A61N 1/36071* (2013.01)

(58) Field of Classification Search
None
See application file for complete search history.

(56) References Cited

U.S. PATENT DOCUMENTS

| | | |
|---|---|---|
| 2,164,121 A | 6/1939 | Pescador |
| 3,363,623 A | 1/1968 | Atwell |
| 3,631,534 A | 12/1971 | Hirota et al. |
| 4,073,296 A | 2/1978 | McCall |
| 4,098,277 A | 7/1978 | Mendell |
| 4,305,402 A | 12/1981 | Katims |
| 4,503,863 A | 3/1985 | Katims |
| 4,573,481 A | 3/1986 | Bullara |
| 4,590,946 A | 5/1986 | Loeb |
| 4,632,095 A | 12/1986 | Libin |
| 4,649,936 A | 3/1987 | Ungar et al. |
| 4,702,254 A | 10/1987 | Zabara |
| 4,840,793 A | 6/1989 | Todd, III et al. |
| 4,867,164 A | 9/1989 | Zabara |
| 4,929,734 A | 5/1990 | Coughenour et al. |
| 4,930,516 A | 6/1990 | Alfano et al. |
| 4,935,234 A | 6/1990 | Todd, III et al. |
| 4,979,511 A | 12/1990 | Terry, Jr. |
| 4,991,578 A | 2/1991 | Cohen |
| 5,019,648 A | 5/1991 | Schlossman et al. |
| 5,025,807 A | 6/1991 | Zabara |
| 5,038,781 A | 8/1991 | Lynch |
| 5,049,659 A | 9/1991 | Cantor et al. |
| 5,073,560 A | 12/1991 | Wu et al. |
| 5,106,853 A | 4/1992 | Showell et al. |
| 5,111,815 A | 5/1992 | Mower |
| 5,154,172 A | 10/1992 | Terry, Jr. et al. |
| 5,175,166 A | 12/1992 | Dunbar et al. |
| 5,179,950 A | 1/1993 | Stanislaw |
| 5,186,170 A | 2/1993 | Varrichio et al. |
| 5,188,104 A | 2/1993 | Wernicke et al. |
| 5,203,326 A | 4/1993 | Collins |
| 5,205,285 A | 4/1993 | Baker, Jr. |
| 5,215,086 A | 6/1993 | Terry, Jr. et al. |
| 5,215,089 A | 6/1993 | Baker, Jr. |
| 5,222,494 A | 6/1993 | Baker, Jr. |
| 5,231,988 A | 8/1993 | Wernicke et al. |
| 5,235,980 A | 8/1993 | Varrichio et al. |
| 5,237,991 A | 8/1993 | Baker et al. |
| 5,251,634 A | 10/1993 | Weinberg |
| 5,263,480 A | 11/1993 | Wernicke et al. |
| 5,269,303 A | 12/1993 | Wernicke et al. |
| 5,299,569 A | 4/1994 | Wernicke et al. |
| 5,304,206 A | 4/1994 | Baker, Jr. et al. |
| 5,330,507 A | 7/1994 | Schwartz |
| 5,330,515 A | 7/1994 | Rutecki et al. |

(Continued)

FOREIGN PATENT DOCUMENTS

| | | |
|---|---|---|
| CN | 201230913 | 5/2009 |
| CN | 101528303 A | 9/2009 |

(Continued)

OTHER PUBLICATIONS

US 6,184,239, 02/2001, Puskas (withdrawn)
Faltys et al.; U.S. Appl. No. 15/153,639 entitled "External programmer," filed May 12, 2016.
Abraham, Coagulation abnormalities in acute lung injury and sepsis, Am. J. Respir. Cell Mol. Biol., vol. 22(4), pp. 401-404, Apr. 2000.
Aekerlund et al., Anti-inflammatory effects of a new tumour necrosis factor-alpha (TNF-Alpha) inhibitor (CNI-1493) in collagen-induced arthritis (CIA) in rats, Clinical & Experimental Immunology, vol. 115, No. 1, pp. 32-41, Jan. 1, 1999.

(Continued)

*Primary Examiner* — Michael Barker
(74) *Attorney, Agent, or Firm* — Shay Glenn LLP

(57) ABSTRACT

Described herein are devices, systems and method of treating inflammation by vagus nerve stimulation and the delivery of an anti-inflammatory drug. In particular, described herein are methods of treating inflammation including the steps of stimulating a subject's inflammatory reflex to inhibit the immune response and administering an anti-inflammatory drug.

11 Claims, 8 Drawing Sheets

(56) References Cited

U.S. PATENT DOCUMENTS

| | | |
|---|---|---|
| 5,335,657 A | 8/1994 | Terry, Jr. et al. |
| 5,344,438 A | 9/1994 | Testerman et al. |
| 5,351,394 A | 10/1994 | Weinberg |
| 5,403,845 A | 4/1995 | Dunbar et al. |
| 5,458,625 A | 10/1995 | Kendall |
| 5,472,841 A | 12/1995 | Jayasena et al. |
| 5,487,756 A | 1/1996 | Kallesoe et al. |
| 5,496,938 A | 3/1996 | Gold et al. |
| 5,503,978 A | 4/1996 | Schneider et al. |
| 5,531,778 A | 7/1996 | Maschino et al. |
| 5,540,730 A | 7/1996 | Terry, Jr. et al. |
| 5,540,734 A | 7/1996 | Zabara |
| 5,567,588 A | 10/1996 | Gold et al. |
| 5,567,724 A | 10/1996 | Kelleher et al. |
| 5,571,150 A | 11/1996 | Wernicke et al. |
| 5,580,737 A | 12/1996 | Polisky et al. |
| 5,582,981 A | 12/1996 | Toole et al. |
| 5,604,231 A | 2/1997 | Smith et al. |
| 5,607,459 A | 3/1997 | Paul et al. |
| 5,611,350 A | 3/1997 | John |
| 5,618,818 A | 4/1997 | Ojo et al. |
| 5,629,285 A | 5/1997 | Black et al. |
| 5,637,459 A | 6/1997 | Burke et al. |
| 5,651,378 A | 7/1997 | Matheny et al. |
| 5,654,151 A | 8/1997 | Allen et al. |
| 5,683,867 A | 11/1997 | Biesecker et al. |
| 5,690,681 A | 11/1997 | Geddes et al. |
| 5,700,282 A | 12/1997 | Zabara |
| 5,705,337 A | 1/1998 | Gold et al. |
| 5,707,400 A | 1/1998 | Terry, Jr. et al. |
| 5,709,853 A | 1/1998 | Lino et al. |
| 5,712,375 A | 1/1998 | Jensen et al. |
| 5,718,912 A | 2/1998 | Thomspon et al. |
| 5,726,017 A | 3/1998 | Lochrie et al. |
| 5,726,179 A | 3/1998 | Messer, Jr. et al. |
| 5,727,556 A | 3/1998 | Weth et al. |
| 5,733,255 A | 3/1998 | Dinh et al. |
| 5,741,802 A | 4/1998 | Kem et al. |
| 5,773,598 A | 6/1998 | Burke et al. |
| 5,786,462 A | 7/1998 | Schneider et al. |
| 5,788,656 A | 8/1998 | Mino |
| 5,792,210 A | 8/1998 | Wamubu et al. |
| 5,853,005 A | 12/1998 | Scanlon |
| 5,854,289 A | 12/1998 | Bianchi et al. |
| 5,902,814 A | 5/1999 | Gordon et al. |
| 5,913,876 A | 6/1999 | Taylor et al. |
| 5,916,239 A | 6/1999 | Geddes et al. |
| 5,919,216 A | 7/1999 | Houben et al. |
| 5,928,272 A | 7/1999 | Adkins et al. |
| 5,964,794 A | 10/1999 | Bolz et al. |
| 5,977,144 A | 11/1999 | Meyer et al. |
| 5,994,330 A | 11/1999 | El Khoury |
| 6,002,964 A | 12/1999 | Feler et al. |
| 6,006,134 A | 12/1999 | Hill et al. |
| 6,017,891 A | 1/2000 | Eibl et al. |
| 6,028,186 A | 2/2000 | Tasset et al. |
| 6,051,017 A | 4/2000 | Loeb et al. |
| 6,083,696 A | 7/2000 | Biesecker et al. |
| 6,083,905 A | 7/2000 | Voorberg et al. |
| 6,096,728 A | 8/2000 | Collins et al. |
| 6,104,956 A | 8/2000 | Naritoku et al. |
| 6,110,900 A | 8/2000 | Gold et al. |
| 6,110,914 A | 8/2000 | Phillips et al. |
| 6,117,837 A | 9/2000 | Tracey et al. |
| 6,124,449 A | 9/2000 | Gold et al. |
| 6,127,119 A | 10/2000 | Stephens et al. |
| 6,140,490 A | 10/2000 | Biesecker et al. |
| 6,141,590 A | 10/2000 | Renirie et al. |
| 6,147,204 A | 11/2000 | Gold et al. |
| 6,159,145 A | 12/2000 | Satoh |
| 6,164,284 A | 12/2000 | Schulman et al. |
| 6,166,048 A | 12/2000 | Bencherif |
| 6,168,778 B1 | 1/2001 | Janjic et al. |
| 6,171,795 B1 | 1/2001 | Korman et al. |
| 6,205,359 B1 | 3/2001 | Boveja |
| 6,208,894 B1 | 3/2001 | Schulman et al. |
| 6,208,902 B1 | 3/2001 | Boveja |
| 6,210,321 B1 | 4/2001 | Di Mino et al. |
| 6,224,862 B1 | 5/2001 | Turecek et al. |
| 6,233,488 B1 | 5/2001 | Hess |
| 6,266,564 B1 | 7/2001 | Hill et al. |
| 6,269,270 B1 | 7/2001 | Boveja |
| 6,304,775 B1 | 10/2001 | Iasemidis et al. |
| 6,308,104 B1 | 10/2001 | Taylor et al. |
| 6,337,997 B1 | 1/2002 | Rise |
| 6,339,725 B1 | 1/2002 | Naritoku et al. |
| 6,341,236 B1 | 1/2002 | Osorio et al. |
| 6,356,787 B1 | 3/2002 | Rezai et al. |
| 6,356,788 B2 | 3/2002 | Boveja |
| 6,381,499 B1 | 4/2002 | Taylor et al. |
| 6,405,732 B1 | 6/2002 | Edwards et al. |
| 6,407,095 B1 | 6/2002 | Lochead et al. |
| 6,428,484 B1 | 8/2002 | Battmer et al. |
| 6,429,217 B1 | 8/2002 | Puskas |
| 6,447,443 B1 | 9/2002 | Keogh et al. |
| 6,449,507 B1 | 9/2002 | Hill et al. |
| 6,473,644 B1 | 10/2002 | Terry, Jr. et al. |
| 6,479,523 B1 | 11/2002 | Puskas |
| 6,487,446 B1 | 11/2002 | Hill et al. |
| 6,511,500 B1 | 1/2003 | Rahme |
| 6,528,529 B1 | 3/2003 | Brann et al. |
| 6,532,388 B1 | 3/2003 | Hill et al. |
| 6,542,774 B2 | 4/2003 | Hill et al. |
| 6,556,868 B2 | 4/2003 | Naritoku et al. |
| 6,564,102 B1 | 5/2003 | Boveja |
| 6,587,719 B1 | 7/2003 | Barrett et al. |
| 6,587,727 B2 | 7/2003 | Osorio et al. |
| 6,600,956 B2 | 7/2003 | Maschino et al. |
| 6,602,891 B2 | 8/2003 | Messer et al. |
| 6,609,025 B2 | 8/2003 | Barrett et al. |
| 6,610,713 B2 | 8/2003 | Tracey |
| 6,611,715 B1 | 8/2003 | Boveja |
| 6,615,081 B1 | 9/2003 | Boveja |
| 6,615,085 B1 | 9/2003 | Boveja |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,628,987 B1 | 9/2003 | Hill et al. |
| 6,633,779 B1 | 10/2003 | Lee et al. |
| 6,656,960 B2 | 12/2003 | Puskas |
| 6,668,191 B1 | 12/2003 | Boveja |
| 6,671,556 B2 | 12/2003 | Osorio et al. |
| 6,684,105 B2 | 1/2004 | Cohen et al. |
| 6,690,973 B2 | 2/2004 | Hill et al. |
| 6,718,208 B2 | 4/2004 | Hill et al. |
| 6,721,603 B2 | 4/2004 | Zabara et al. |
| 6,735,471 B2 | 5/2004 | Hill et al. |
| 6,735,475 B1 | 5/2004 | Whitehurst et al. |
| 6,760,626 B1 | 7/2004 | Boveja |
| 6,778,854 B2 | 8/2004 | Puskas |
| 6,804,558 B2 | 10/2004 | Haller et al. |
| RE38,654 E | 11/2004 | Hill et al. |
| 6,826,428 B1 | 11/2004 | Chen et al. |
| 6,832,114 B1 | 12/2004 | Whitehurst et al. |
| 6,838,471 B2 | 1/2005 | Tracey |
| RE38,705 E | 2/2005 | Hill et al. |
| 6,879,859 B1 | 4/2005 | Boveja |
| 6,885,888 B2 | 4/2005 | Rezai |
| 6,901,294 B1 | 5/2005 | Whitehurst et al. |
| 6,904,318 B2 | 6/2005 | Hill et al. |
| 6,920,357 B2 | 7/2005 | Osorio et al. |
| 6,928,320 B2 | 8/2005 | King |
| 6,934,583 B2 | 8/2005 | Weinberg et al. |
| 6,937,903 B2 | 8/2005 | Schuler et al. |
| 6,961,618 B2 | 11/2005 | Osorio et al. |
| 6,978,787 B1 | 12/2005 | Broniatowski |
| 7,011,638 B2 | 3/2006 | Schuler et al. |
| 7,054,686 B2 | 5/2006 | MacDonald |
| 7,054,692 B1 | 5/2006 | Whitehurst et al. |
| 7,058,447 B2 | 6/2006 | Hill et al. |
| 7,062,320 B2 | 6/2006 | Ehlinger, Jr. |
| 7,069,082 B2 | 6/2006 | Lindenthaler |
| 7,072,720 B2 | 7/2006 | Puskas |
| 7,076,307 B2 | 7/2006 | Boveja et al. |

(56) References Cited

U.S. PATENT DOCUMENTS

| | | |
|---|---|---|
| 7,142,910 B2 | 11/2006 | Puskas |
| 7,142,917 B2 | 11/2006 | Fukui |
| 7,149,574 B2 | 12/2006 | Yun et al. |
| 7,155,279 B2 | 12/2006 | Whitehurst et al. |
| 7,155,284 B1 | 12/2006 | Whitehurst et al. |
| 7,167,750 B2 | 1/2007 | Knudson et al. |
| 7,167,751 B1 | 1/2007 | Whitehurst et al. |
| 7,174,218 B1 | 2/2007 | Kuzma |
| 7,184,828 B2 | 2/2007 | Hill et al. |
| 7,184,829 B2 | 2/2007 | Hill et al. |
| 7,191,012 B2 | 3/2007 | Boveja et al. |
| 7,204,815 B2 | 4/2007 | Connor |
| 7,209,787 B2 | 4/2007 | DiLorenzo |
| 7,225,019 B2 | 5/2007 | Jahns et al. |
| 7,228,167 B2 | 6/2007 | Kara et al. |
| 7,238,715 B2 | 7/2007 | Tracey et al. |
| 7,242,984 B2 | 7/2007 | DiLorenzo |
| 7,269,457 B2 | 9/2007 | Shafer et al. |
| 7,345,178 B2 | 3/2008 | Nunes et al. |
| 7,467,016 B2 | 12/2008 | Colborn |
| 7,544,497 B2 | 6/2009 | Sinclair et al. |
| 7,561,918 B2 | 7/2009 | Armstrong et al. |
| 7,711,432 B2 | 5/2010 | Thimineur et al. |
| 7,729,760 B2 | 6/2010 | Patel et al. |
| 7,751,891 B2 | 7/2010 | Armstrong et al. |
| 7,776,326 B2 | 8/2010 | Milbrandt et al. |
| 7,797,058 B2 | 9/2010 | Mrva et al. |
| 7,819,883 B2 | 10/2010 | Westlund et al. |
| 7,822,486 B2 | 10/2010 | Foster et al. |
| 7,829,556 B2 | 11/2010 | Bemis et al. |
| 7,869,885 B2 | 1/2011 | Begnaud et al. |
| 7,937,145 B2 | 5/2011 | Dobak |
| 7,962,220 B2 | 6/2011 | Kolafa et al. |
| 7,974,701 B2 | 7/2011 | Armstrong |
| 7,974,707 B2 | 7/2011 | Inman |
| 7,996,088 B2 | 8/2011 | Marrosu et al. |
| 7,996,092 B2 | 8/2011 | Mrva et al. |
| 8,019,419 B1 | 9/2011 | Panescu et al. |
| 8,103,349 B2 | 1/2012 | Donders et al. |
| 8,165,668 B2 | 4/2012 | Dacey, Jr. et al. |
| 8,180,446 B2 | 5/2012 | Dacey, Jr. et al. |
| 8,195,287 B2 | 6/2012 | Dacey, Jr. et al. |
| 8,214,056 B2 | 7/2012 | Hoffer et al. |
| 8,233,982 B2 | 7/2012 | Libbus |
| 8,391,970 B2 | 3/2013 | Tracey et al. |
| 8,412,338 B2 | 4/2013 | Faltys |
| 8,571,654 B2 | 10/2013 | Libbus et al. |
| 8,577,458 B1 | 11/2013 | Libbus et al. |
| 8,600,505 B2 | 12/2013 | Libbus et al. |
| 8,612,002 B2 | 12/2013 | Faltys et al. |
| 8,630,709 B2 | 1/2014 | Libbus et al. |
| 8,688,212 B2 | 4/2014 | Libbus et al. |
| 8,700,150 B2 | 4/2014 | Libbus et al. |
| 8,729,129 B2 | 5/2014 | Tracey et al. |
| 8,788,034 B2 | 7/2014 | Levine et al. |
| 8,843,210 B2 | 9/2014 | Simon et al. |
| 8,855,767 B2 | 10/2014 | Faltys et al. |
| 8,886,339 B2 | 11/2014 | Faltys et al. |
| 8,914,114 B2 | 12/2014 | Tracey et al. |
| 8,918,178 B2 | 12/2014 | Simon et al. |
| 8,918,191 B2 | 12/2014 | Libbus et al. |
| 8,923,964 B2 | 12/2014 | Libbus et al. |
| 8,983,628 B2 | 3/2015 | Simon et al. |
| 8,983,629 B2 | 3/2015 | Simon et al. |
| 8,996,116 B2 | 3/2015 | Faltys et al. |
| 9,114,262 B2 | 8/2015 | Libbus et al. |
| 9,162,064 B2 | 10/2015 | Faltys et al. |
| 9,174,041 B2 | 11/2015 | Faltys et al. |
| 9,211,409 B2 | 12/2015 | Tracey et al. |
| 9,211,410 B2 | 12/2015 | Levine et al. |
| 9,254,383 B2 | 2/2016 | Simon et al. |
| 9,272,143 B2 | 3/2016 | Libbus et al. |
| 9,358,381 B2 | 6/2016 | Simon et al. |
| 9,399,134 B2 | 7/2016 | Simon et al. |
| 9,403,001 B2 | 8/2016 | Simon et al. |
| 9,409,024 B2 | 8/2016 | KenKnight et al. |
| 9,415,224 B2 | 8/2016 | Libbus et al. |
| 9,452,290 B2 | 9/2016 | Libbus et al. |
| 9,504,832 B2 | 11/2016 | Libbus et al. |
| 9,511,228 B2 | 12/2016 | Amurthur et al. |
| 9,533,153 B2 | 1/2017 | Libbus et al. |
| 2001/0002441 A1 | 5/2001 | Boveja |
| 2002/0026141 A1 | 2/2002 | Houben et al. |
| 2002/0040035 A1 | 4/2002 | Myers et al. |
| 2002/0077675 A1 | 6/2002 | Greenstein |
| 2002/0086871 A1 | 7/2002 | O'Neill et al. |
| 2002/0095139 A1 | 7/2002 | Keogh et al. |
| 2002/0099417 A1 | 7/2002 | Naritoku et al. |
| 2002/0138075 A1 | 9/2002 | Edwards et al. |
| 2002/0138109 A1 | 9/2002 | Keogh et al. |
| 2002/0193859 A1 | 12/2002 | Schulman et al. |
| 2002/0198570 A1 | 12/2002 | Puskas |
| 2003/0018367 A1 | 1/2003 | DiLorenzo |
| 2003/0045909 A1 | 3/2003 | Gross et al. |
| 2003/0088301 A1 | 5/2003 | King |
| 2003/0191404 A1 | 10/2003 | Klein |
| 2003/0194752 A1 | 10/2003 | Anderson et al. |
| 2003/0195578 A1 | 10/2003 | Perron et al. |
| 2003/0212440 A1 | 11/2003 | Boveja |
| 2003/0229380 A1 | 12/2003 | Adams et al. |
| 2003/0236557 A1 | 12/2003 | Whitehurst et al. |
| 2003/0236558 A1 | 12/2003 | Whitehurst et al. |
| 2004/0015202 A1 | 1/2004 | Chandler et al. |
| 2004/0015205 A1 | 1/2004 | Whitehurst et al. |
| 2004/0024422 A1 | 2/2004 | Hill et al. |
| 2004/0024428 A1 | 2/2004 | Barrett et al. |
| 2004/0024439 A1 | 2/2004 | Riso |
| 2004/0030362 A1 | 2/2004 | Hill et al. |
| 2004/0039427 A1 | 2/2004 | Barrett et al. |
| 2004/0048795 A1 | 3/2004 | Ivanova et al. |
| 2004/0049121 A1 | 3/2004 | Yaron |
| 2004/0059383 A1 | 3/2004 | Puskas |
| 2004/0111139 A1 | 6/2004 | McCreery et al. |
| 2004/0138517 A1 | 7/2004 | Osorio et al. |
| 2004/0138518 A1 | 7/2004 | Rise et al. |
| 2004/0138536 A1 | 7/2004 | Frei et al. |
| 2004/0146949 A1 | 7/2004 | Tan et al. |
| 2004/0153127 A1 | 8/2004 | Gordon et al. |
| 2004/0158119 A1 | 8/2004 | Osorio et al. |
| 2004/0162584 A1 | 8/2004 | Hill et al. |
| 2004/0172074 A1 | 9/2004 | Yoshihito |
| 2004/0172085 A1 | 9/2004 | Knudson et al. |
| 2004/0172086 A1 | 9/2004 | Knudson et al. |
| 2004/0172088 A1 | 9/2004 | Knudson et al. |
| 2004/0172094 A1 | 9/2004 | Cohen et al. |
| 2004/0176812 A1 | 9/2004 | Knudson et al. |
| 2004/0178706 A1 | 9/2004 | D'Orso |
| 2004/0193231 A1 | 9/2004 | David et al. |
| 2004/0199209 A1 | 10/2004 | Hill et al. |
| 2004/0199210 A1 | 10/2004 | Shelchuk |
| 2004/0204355 A1 | 10/2004 | Tracey et al. |
| 2004/0215287 A1 | 10/2004 | Swoyer et al. |
| 2004/0236381 A1 | 11/2004 | Dinsmoor et al. |
| 2004/0236382 A1 | 11/2004 | Dinsmoor et al. |
| 2004/0240691 A1 | 12/2004 | Grafenberg |
| 2004/0243182 A1 | 12/2004 | Cohen et al. |
| 2004/0254612 A1 | 12/2004 | Ezra et al. |
| 2004/0267152 A1 | 12/2004 | Pineda |
| 2005/0021092 A1 | 1/2005 | Yun et al. |
| 2005/0021101 A1 | 1/2005 | Chen et al. |
| 2005/0027328 A1 | 2/2005 | Greenstein |
| 2005/0043774 A1 | 2/2005 | Devlin et al. |
| 2005/0049655 A1 | 3/2005 | Boveja et al. |
| 2005/0065553 A1 | 3/2005 | Ben Ezra et al. |
| 2005/0065573 A1 | 3/2005 | Rezai |
| 2005/0065575 A1 | 3/2005 | Dobak |
| 2005/0070970 A1 | 3/2005 | Knudson et al. |
| 2005/0070974 A1 | 3/2005 | Knudson et al. |
| 2005/0075701 A1 | 4/2005 | Shafer |
| 2005/0075702 A1 | 4/2005 | Shafer |
| 2005/0095246 A1 | 5/2005 | Shafer |
| 2005/0096707 A1 | 5/2005 | Hill et al. |
| 2005/0131467 A1 | 6/2005 | Boveja |
| 2005/0131486 A1 | 6/2005 | Boveja et al. |

(56) References Cited

U.S. PATENT DOCUMENTS

| | | |
|---|---|---|
| 2005/0131487 A1 | 6/2005 | Boveja |
| 2005/0131493 A1 | 6/2005 | Boveja et al. |
| 2005/0137644 A1 | 6/2005 | Boveja et al. |
| 2005/0137645 A1 | 6/2005 | Voipio et al. |
| 2005/0143781 A1 | 6/2005 | Carbunaru et al. |
| 2005/0143787 A1 | 6/2005 | Boveja et al. |
| 2005/0149126 A1 | 7/2005 | Libbus |
| 2005/0149129 A1 | 7/2005 | Libbus et al. |
| 2005/0149131 A1 | 7/2005 | Libbus et al. |
| 2005/0153885 A1 | 7/2005 | Yun et al. |
| 2005/0154425 A1 | 7/2005 | Boveja et al. |
| 2005/0154426 A1 | 7/2005 | Boveja et al. |
| 2005/0165458 A1 | 7/2005 | Boveja et al. |
| 2005/0177200 A1 | 8/2005 | George et al. |
| 2005/0182288 A1 | 8/2005 | Zabara |
| 2005/0182467 A1 | 8/2005 | Hunter et al. |
| 2005/0187584 A1 | 8/2005 | Denker et al. |
| 2005/0187586 A1 | 8/2005 | David et al. |
| 2005/0187590 A1 | 8/2005 | Boveja et al. |
| 2005/0192644 A1 | 9/2005 | Boveja et al. |
| 2005/0197600 A1 | 9/2005 | Schuler et al. |
| 2005/0197675 A1 | 9/2005 | David et al. |
| 2005/0197678 A1 | 9/2005 | Boveja et al. |
| 2005/0203501 A1 | 9/2005 | Aldrich et al. |
| 2005/0209654 A1 | 9/2005 | Boveja et al. |
| 2005/0216064 A1 | 9/2005 | Heruth et al. |
| 2005/0216070 A1 | 9/2005 | Boveja et al. |
| 2005/0216071 A1 | 9/2005 | Devlin et al. |
| 2005/0240229 A1 | 10/2005 | Whitehurst et al. |
| 2005/0240231 A1 | 10/2005 | Aldrich et al. |
| 2005/0240241 A1 | 10/2005 | Yun et al. |
| 2005/0251220 A1 | 11/2005 | Barrett et al. |
| 2005/0251222 A1 | 11/2005 | Barrett et al. |
| 2005/0267542 A1 | 12/2005 | David et al. |
| 2005/0267547 A1 | 12/2005 | Knudson et al. |
| 2005/0283198 A1 | 12/2005 | Haubrich et al. |
| 2006/0009815 A1 | 1/2006 | Boveja et al. |
| 2006/0015151 A1 | 1/2006 | Aldrich |
| 2006/0025828 A1 | 2/2006 | Armstrong et al. |
| 2006/0036293 A1 | 2/2006 | Whitehurst et al. |
| 2006/0052657 A9 | 3/2006 | Zabara |
| 2006/0052831 A1 | 3/2006 | Fukui |
| 2006/0052836 A1 | 3/2006 | Kim et al. |
| 2006/0058851 A1 | 3/2006 | Cigaina |
| 2006/0064137 A1 | 3/2006 | Stone |
| 2006/0064139 A1 | 3/2006 | Chung et al. |
| 2006/0074450 A1 | 4/2006 | Boveja et al. |
| 2006/0074473 A1 | 4/2006 | Gertner |
| 2006/0079936 A1 | 4/2006 | Boveja et al. |
| 2006/0085046 A1 | 4/2006 | Rezai et al. |
| 2006/0095081 A1 | 5/2006 | Zhou et al. |
| 2006/0095090 A1 | 5/2006 | De Ridder |
| 2006/0100668 A1 | 5/2006 | Ben-David et al. |
| 2006/0106755 A1 | 5/2006 | Stuhec |
| 2006/0111644 A1 | 5/2006 | Guttag et al. |
| 2006/0111754 A1 | 5/2006 | Rezai et al. |
| 2006/0111755 A1 | 5/2006 | Stone et al. |
| 2006/0116739 A1 | 6/2006 | Betser et al. |
| 2006/0122675 A1 | 6/2006 | Libbus et al. |
| 2006/0129200 A1 | 6/2006 | Kurokawa |
| 2006/0129202 A1 | 6/2006 | Armstrong |
| 2006/0135998 A1 | 6/2006 | Libbus et al. |
| 2006/0142802 A1 | 6/2006 | Armstrong |
| 2006/0142822 A1 | 6/2006 | Tulgar |
| 2006/0149337 A1 | 7/2006 | John |
| 2006/0161216 A1 | 7/2006 | John et al. |
| 2006/0161217 A1 | 7/2006 | Jaax et al. |
| 2006/0167497 A1 | 7/2006 | Armstrong et al. |
| 2006/0167498 A1 | 7/2006 | DiLorenzo |
| 2006/0167501 A1 | 7/2006 | Ben-David et al. |
| 2006/0173493 A1 | 8/2006 | Armstrong et al. |
| 2006/0173508 A1 | 8/2006 | Stone et al. |
| 2006/0178691 A1 | 8/2006 | Binmoeller |
| 2006/0178703 A1 | 8/2006 | Huston et al. |
| 2006/0178706 A1 | 8/2006 | Lisogurski et al. |
| 2006/0190044 A1 | 8/2006 | Libbus et al. |
| 2006/0200208 A1 | 9/2006 | Terry, Jr. et al. |
| 2006/0200219 A1 | 9/2006 | Thrope et al. |
| 2006/0206155 A1 | 9/2006 | Ben-David et al. |
| 2006/0206158 A1 | 9/2006 | Wu et al. |
| 2006/0229677 A1 | 10/2006 | Moffitt et al. |
| 2006/0229681 A1 | 10/2006 | Fischell |
| 2006/0241699 A1 | 10/2006 | Libbus et al. |
| 2006/0247719 A1 | 11/2006 | Maschino et al. |
| 2006/0247721 A1 | 11/2006 | Maschino et al. |
| 2006/0247722 A1 | 11/2006 | Maschino et al. |
| 2006/0259077 A1 | 11/2006 | Pardo et al. |
| 2006/0259084 A1 | 11/2006 | Zhang et al. |
| 2006/0259085 A1 | 11/2006 | Zhang et al. |
| 2006/0259107 A1 | 11/2006 | Caparso et al. |
| 2006/0271115 A1 | 11/2006 | Ben-Ezra et al. |
| 2006/0282121 A1 | 12/2006 | Payne et al. |
| 2006/0282131 A1 | 12/2006 | Caparso et al. |
| 2006/0282145 A1 | 12/2006 | Caparso et al. |
| 2006/0287678 A1 | 12/2006 | Shafer |
| 2006/0287679 A1 | 12/2006 | Stone |
| 2006/0292099 A1 | 12/2006 | Milburn et al. |
| 2006/0293720 A1 | 12/2006 | DiLorenzo |
| 2006/0293721 A1 | 12/2006 | Tarver et al. |
| 2006/0293723 A1 | 12/2006 | Whitehurst et al. |
| 2007/0016262 A1 | 1/2007 | Gross et al. |
| 2007/0016263 A1 | 1/2007 | Armstrong et al. |
| 2007/0021785 A1 | 1/2007 | Inman et al. |
| 2007/0021786 A1 | 1/2007 | Parnis et al. |
| 2007/0021814 A1 | 1/2007 | Inman et al. |
| 2007/0025608 A1 | 2/2007 | Armstrong |
| 2007/0027482 A1 | 2/2007 | Parnis et al. |
| 2007/0027483 A1 | 2/2007 | Maschino et al. |
| 2007/0027484 A1 | 2/2007 | Guzman et al. |
| 2007/0027486 A1 | 2/2007 | Armstrong |
| 2007/0027492 A1 | 2/2007 | Maschino et al. |
| 2007/0027496 A1 | 2/2007 | Parnis et al. |
| 2007/0027497 A1 | 2/2007 | Parnis |
| 2007/0027498 A1 | 2/2007 | Maschino et al. |
| 2007/0027499 A1 | 2/2007 | Maschino et al. |
| 2007/0027500 A1 | 2/2007 | Maschino et al. |
| 2007/0027504 A1 | 2/2007 | Barrett et al. |
| 2007/0055324 A1 | 3/2007 | Thompson et al. |
| 2007/0067004 A1 | 3/2007 | Boveja et al. |
| 2007/0083242 A1 | 4/2007 | Mazgalev et al. |
| 2007/0093434 A1 | 4/2007 | Rossetti et al. |
| 2007/0093870 A1 | 4/2007 | Maschino |
| 2007/0093875 A1 | 4/2007 | Chavan et al. |
| 2007/0100263 A1 | 5/2007 | Merfeld |
| 2007/0100377 A1 | 5/2007 | Armstrong et al. |
| 2007/0100378 A1 | 5/2007 | Maschino |
| 2007/0100380 A1 | 5/2007 | Fukui |
| 2007/0100392 A1 | 5/2007 | Maschino et al. |
| 2007/0106339 A1 | 5/2007 | Errico et al. |
| 2007/0112404 A1 | 5/2007 | Mann et al. |
| 2007/0118177 A1 | 5/2007 | Libbus et al. |
| 2007/0118178 A1 | 5/2007 | Fukui |
| 2007/0129780 A1 | 6/2007 | Whitehurst et al. |
| 2007/0135846 A1 | 6/2007 | Knudson et al. |
| 2007/0135856 A1 | 6/2007 | Knudson et al. |
| 2007/0135857 A1 | 6/2007 | Knudson et al. |
| 2007/0135858 A1 | 6/2007 | Knudson et al. |
| 2007/0142870 A1 | 6/2007 | Knudson et al. |
| 2007/0142871 A1 | 6/2007 | Libbus et al. |
| 2007/0142874 A1 | 6/2007 | John |
| 2007/0150006 A1 | 6/2007 | Libbus et al. |
| 2007/0150011 A1 | 6/2007 | Meyer et al. |
| 2007/0150021 A1 | 6/2007 | Chen et al. |
| 2007/0150027 A1 | 6/2007 | Rogers |
| 2007/0156180 A1 | 7/2007 | Jaax et al. |
| 2007/0198063 A1 | 8/2007 | Hunter et al. |
| 2007/0239243 A1 | 10/2007 | Moffitt et al. |
| 2007/0244522 A1 | 10/2007 | Overstreet |
| 2007/0250145 A1 | 10/2007 | Kraus et al. |
| 2007/0255320 A1 | 11/2007 | Inman et al. |
| 2007/0255333 A1 | 11/2007 | Giftakis |
| 2007/0255339 A1 | 11/2007 | Torgerson |
| 2008/0021517 A1 | 1/2008 | Dietrich |
| 2008/0021520 A1 | 1/2008 | Dietrich |

(56) References Cited

U.S. PATENT DOCUMENTS

| | | |
|---|---|---|
| 2008/0046055 A1 | 2/2008 | Durand et al. |
| 2008/0058871 A1 | 3/2008 | Libbus et al. |
| 2008/0103407 A1 | 5/2008 | Bolea et al. |
| 2008/0140138 A1 | 6/2008 | Ivanova et al. |
| 2008/0183226 A1 | 7/2008 | Buras et al. |
| 2008/0183246 A1 | 7/2008 | Patel et al. |
| 2008/0208266 A1 | 8/2008 | Lesser et al. |
| 2008/0234790 A1 | 9/2008 | Bayer et al. |
| 2008/0249439 A1 | 10/2008 | Tracey et al. |
| 2008/0281365 A1 | 11/2008 | Tweden et al. |
| 2008/0281372 A1 | 11/2008 | Libbus et al. |
| 2009/0012590 A1 | 1/2009 | Inman et al. |
| 2009/0048194 A1 | 2/2009 | Aerssens et al. |
| 2009/0082832 A1 | 3/2009 | Carbunaru et al. |
| 2009/0105782 A1 | 4/2009 | Mickle et al. |
| 2009/0123521 A1 | 5/2009 | Weber et al. |
| 2009/0125079 A1 | 5/2009 | Armstrong et al. |
| 2009/0143831 A1 | 6/2009 | Huston et al. |
| 2009/0171405 A1 | 7/2009 | Craig |
| 2009/0177112 A1 | 7/2009 | Gharib et al. |
| 2009/0187231 A1 | 7/2009 | Errico et al. |
| 2009/0248097 A1 | 10/2009 | Tracey et al. |
| 2009/0254143 A1 | 10/2009 | Tweden et al. |
| 2009/0275997 A1 | 11/2009 | Faltys et al. |
| 2009/0276019 A1 | 11/2009 | Perez et al. |
| 2009/0281593 A9 | 11/2009 | Errico et al. |
| 2010/0003656 A1 | 1/2010 | Kilgard et al. |
| 2010/0010603 A1 | 1/2010 | Ben-David et al. |
| 2010/0042186 A1 | 2/2010 | Ben-David et al. |
| 2010/0063563 A1 | 3/2010 | Craig |
| 2010/0074934 A1 | 3/2010 | Hunter |
| 2010/0191304 A1 | 7/2010 | Scott |
| 2010/0215632 A1 | 8/2010 | Boss et al. |
| 2010/0241183 A1 | 9/2010 | DiLorenzo |
| 2010/0249859 A1 | 9/2010 | DiLorenzo |
| 2010/0280562 A1 | 11/2010 | Pi et al. |
| 2010/0280569 A1 | 11/2010 | Bobillier et al. |
| 2011/0004266 A1 | 1/2011 | Sharma |
| 2011/0054569 A1 | 3/2011 | Zitnik et al. |
| 2011/0066208 A1 | 3/2011 | Pasricha et al. |
| 2011/0082515 A1 | 4/2011 | Libbus et al. |
| 2011/0092882 A1 | 4/2011 | Firlik et al. |
| 2011/0144717 A1 | 6/2011 | Burton et al. |
| 2011/0307027 A1 | 12/2011 | Sharma et al. |
| 2012/0065706 A1 | 3/2012 | Vallapureddy et al. |
| 2012/0185009 A1 | 7/2012 | Kornet et al. |
| 2012/0185020 A1 | 7/2012 | Simon et al. |
| 2013/0066392 A1 | 3/2013 | Simon et al. |
| 2013/0066395 A1 | 3/2013 | Simon et al. |
| 2013/0079834 A1 | 3/2013 | Levine |
| 2013/0245718 A1 | 9/2013 | Birkholz et al. |
| 2013/0253413 A1 | 9/2013 | Levine et al. |
| 2013/0317580 A1 | 11/2013 | Simon et al. |
| 2014/0330335 A1 | 11/2014 | Errico et al. |
| 2015/0100100 A1 | 4/2015 | Tracey et al. |
| 2015/0241447 A1 | 8/2015 | Zitnik et al. |
| 2016/0038745 A1 | 2/2016 | Faltys et al. |
| 2016/0051813 A1 | 2/2016 | Faltys et al. |
| 2016/0367808 A9 | 12/2016 | Simon et al. |

FOREIGN PATENT DOCUMENTS

| | | |
|---|---|---|
| CN | 101578067 A | 11/2009 |
| CN | 101868280 A | 10/2010 |
| DE | 2628045 A1 | 1/1977 |
| DE | 3736664 A1 | 5/1989 |
| DE | 20316509 U1 | 4/2004 |
| EP | 0438510 B1 | 8/1996 |
| EP | 0726791 B1 | 6/2000 |
| EP | 1001827 B1 | 1/2004 |
| EP | 2213330 A2 | 8/2010 |
| EP | 2073896 B1 | 10/2011 |
| GB | 04133 | 2/1910 |
| WO | WO93/01862 A1 | 2/1993 |
| WO | WO97/30998 A1 | 8/1997 |
| WO | WO98/20868 A1 | 5/1998 |
| WO | WO00/27381 A2 | 5/2000 |
| WO | WO00/47104 A2 | 8/2000 |
| WO | WO01/00273 A1 | 1/2001 |
| WO | WO01/08617 A1 | 2/2001 |
| WO | WO01/89526 A1 | 11/2001 |
| WO | WO02/44176 A1 | 6/2002 |
| WO | WO02/057275 A1 | 7/2002 |
| WO | WO03/072135 A2 | 9/2003 |
| WO | WO2004/000413 A2 | 12/2003 |
| WO | WO2004/064918 A1 | 8/2004 |
| WO | WO2006/073484 A1 | 7/2006 |
| WO | WO2006/076681 A2 | 7/2006 |
| WO | WO2007/133718 A2 | 11/2007 |
| WO | WO2010/005482 A1 | 1/2010 |
| WO | WO2010/067360 A2 | 6/2010 |

OTHER PUBLICATIONS

Anderson et al.; Reflex principles of immunological homeostasis; Annu. Rev. Immunol.; 30; pp. 313-335; Apr. 2012.

Antonica, A., et al., Vagal control of lymphocyte release from rat thymus, J. Auton. Nerv. Syst., vol. 48(3), pp. 187-197, Aug. 1994.

Asakura et al., Non-surgical therapy for ulcerative colitis, Nippon Geka Gakkai Zasshi, vol. 98, No. 4, pp. 431-437, Apr. 1997 (abstract only).

Beliavskaia et al.,"On the effects of prolonged stimulation of the peripheral segment of the vagus nerve . . . ," Fiziologicheskii Zhurnal SSSR Imeni I.M. Sechenova., vol. 52(11); p. 1315-1321, Nov. 1966.

Ben-Noun et al.; Neck circumference as a simple screening measure for identifying overweight and obese patients; Obesity Research; vol. 9; No. 8; pp. 470-477; Aug. 8, 2001.

Benoist, et al., "Mast cells in autoimmune disease" Nature., vol. 420(19): pp. 875-878, Dec. 2002.

Benthem et al.; Parasympathetic inhibition of sympathetic neural activity to the pancreas; Am.J.Physiol Endocrinol.Metab; 280(2); pp. E378-E381; Feb. 2001.

Bernik et al., Vagus nerve stimulation attenuates cardiac TNF production in endotoxic shock, (supplemental to Shock, vol. 15, 2001, Injury, inflammation and sepsis: laboratory and clinical approaches, SHOCK, Abstracts, 24th Annual Conference on Shock, Marco Island, FL, Jun. 9-12, 2001), Abstract No. 81.

Bernik et al., Vagus nerve stimulation attenuates endotoxic shock and cardiac TNF production, 87th Clinical Congress of the American College of Surgeons, New Orleans, LA, Oct. 9, 2001.

Bernik et al., Vagus nerve stimulation attenuates LPS-induced cardiac TNF production and myocardial depression in shock, New York Surgical Society, New York, NY, Apr. 11, 2001.

Bernik, et al., Pharmacological stimulation of the cholinergic antiinflammatory pathway, The Journal of Experimental Medicine, vol. 195, No. 6, pp. 781-788, Mar. 18, 2002.

Besedovsky, H., et al., Immunoregulatory feedback between interleukin-1 and glucocorticoid hormones, Science, vol. 233, No. 4764, pp. 652-654, Aug. 1986.

Bhattacharya, S.K. et al., Central muscarinic receptor subtypes and carrageenin-induced paw oedema in rats, Res. Esp. Med. vol. 191(1), pp. 65-76, Dec. 1991.

Bianchi et al., Suppression of proinflammatory cytokines in monocytes by a tetravalent guanylhydrazone, Journal of Experimental Medicine, vol. 183, pp. 927-936, Mar. 1996.

Biggio et al.; Chronic vagus nerve stimulation induces neuronal plasticity in the rat hippocampus; Int. J. Neurpsychopharmacol.; vol. 12; No. 9; pp. 1209-1221; Oct. 2009.

Blackwell, T. S. et al., Sepsis and cytokines: current status, Br. J. Anaesth., vol. 77(1), pp. 110-117, Jul. 1996.

Blum, A. et al., Role of cytokines in heart failure, Am. Heart J., vol. 135(2), pp. 181-186, Feb. 1998.

Boldyreff, Gastric and intestinal mucus, its properties and physiological importance, Acta Medica Scandinavica (journal), vol. 89, Issue 1-2, pp. 1-14, Jan./Dec. 1936.

Borovikova et al., Acetylcholine inhibition of immune response to bacterial endotoxin in human macrophages, Abstracts, Society for Neuroscience, 29th Annual Meeting, Miami Beach, FL, (Abs. No. 624.6); Oct. 23-28, 1999.

(56) References Cited

OTHER PUBLICATIONS

Borovikova et al., Efferent vagus nerve activity attenuates cytokine-mediated inflammation, Society for Neuroscience Abstracts, vol. 26, No. 102, Nov. 4-9, 2000 (abstract only).

Borovikova et al., Intracerebroventricular CNI-1493 prevents LPS-induced hypotension and peak serum TNF at a four-log lower dose than systemic treatment, 21st Annual Conference on Shock, San Antonio, TX, Jun. 14-17, 1998, Abstract No. 86.

Borovikova et al., Role of the efferent vagus nerve signaling in the regulation of the innate immune response to LPS, (supplemental to SHOCK, vol. 13, 2000, Molecular, cellular, and systemic pathobiological aspects and therapeutic approaches, abstracts, 5th world congress on Trauma, Shock inflammation and sepsis-pathophysiology, immune consequences and therapy, Feb. 29, 2000-Mar. 4, 2000, Munich, DE), Abstract No. 166.

Borovikova et al., Role of the vagus nerve in the anti-inflammatory effects of CNI-1493, the FASEB journal, vol. 14, No. 4, 2000 (Experimental Biology 2000, San Diego, CA, Apr. 15-18, 2000, Abstract No. 97.9).

Borovikova et al., Vagotomy blocks the protective effects of I.C.V. CNI-1493 against LPS-induced shock, (Supplemental to SHOCK, vol. 11, 1999, Molecular, cellular, and systemic pathobioloigal aspects and therapeutic approaches, abstacts and program, Fourth International Shock Congress and 22nd Annual Conference on Shock, Philadelphia, PA, Jun. 12-16, 1999), Abstract No. 277.

Borovikova, L. V., et al., Role of vagus nerve signaling in CNI-1493-mediated suppression of acute inflammation, Autonomic Neuroscience, vol. 85, No. 1-3, pp. 141-147, Dec. 20, 2000.

Borovikova, L. V., et al., Vagus nerve stimulation attenuates the systemic inflammatory response to endotoxin, Nature, vol. 405, No. 6785: pp. 458-462, May 25, 2000.

Bruchfeld et al.; Whole blood cytokine attenuation by cholinergic agonists ex vivo and relationship to vagus nerve activity in rheumatoid arthritis; J. Int. Med.; 268(1); pp. 94-101; Jul. 2010.

Bulloch et al.; Characterization of choline O-acetyltransferase (ChAT) in the BALB/C mouse spleen; Int.J.Neurosci.; 76(1-2); pp. 141-149; May 1994.

Bumgardner, G. L. et al., Transplantation and cytokines, Seminars in Liver Disease, vol. 19, No. 2, pp. 189-204, (year of pub. Sufficiently earlier than effective US filing date and any foreign priority date) 1999.

Burke et al., Bent pseudoknots and novel RNA inhibitors of type 1 human immunodeficiency virus (HIV-1) reverse transcriptase, J. Mol. Biol., vol. 264(4); pp. 650-666, Dec. 1996.

Bushby et al; Centiles for adult head circumference; Archives of Disease in Childhood; vol. 67(10); pp. 1286-1287; Oct. 1992.

Cano et al.; Characterization of the central nervous system innervation of the rat spleen using viral transneuronal tracing; J.Comp Neurol.; 439(1); pp. 1-18; Oct. 2001.

Carteron, N. L., Cytokines in rheumatoid arthritis: trials and tribulations, Mol. Med. Today, vol. 6(8), pp. 315-323, Aug. 2000.

Cheyuo et al.; The parasympathetic nervous system in the quest for stroke therapeutics; J. Cereb. Blood Flow Metab.; 31(5); pp. 1187-1195; May 2011.

Cicala et al., "Linkage between inflammation and coagulation: An update on the molecular basis of the crosstalk," Life Sciences, vol. 62(20); pp. 1817-1824, Apr. 1998.

Clark et al.; Enhanced recognition memory following vagus nerve stimulation in human subjects; Nat. Neurosci.; 2(1); pp. 94-98; Jan. 1999.

Cohen, "The immunopathogenesis of sepsis," Nature., vol. 420(6917): pp. 885-891, Dec. 2002.

Corcoran, et al., The effects of vagus nerve stimulation on pro- and anti-inflammatory cytokines in humans: a preliminary report, NeuroImmunoModulation, vol. 12(5), pp. 307-309, Sep. 2005.

Dake; Chronic cerebrospinal venous insufficiency and multiple sclerosis: Hostory and background; Techniques Vasc. Intervent. Radiol.; 15(2); pp. 94-100; Jun. 2012.

Das, Critical advances in spticemia and septic shock, Critical Care, vol. 4, pp. 290-296, Sep. 7, 2000.

Del Signore et al; Nicotinic acetylcholine receptor subtypes in the rat sympathetic ganglion: pharmacological characterization, subcellular distribution and effect of pre- and postganglionic nerve crush; J.Neuropathol.Exp.Neurol.; 63(2); pp. 138-150; Feb. 2004.

Diamond et al.; Mapping the immunological homunculus; Proc. Natl. Acad. Sci. USA; 108(9); pp. 3461-3462; Mar. 1, 2011.

Dibbs, Z., et al., Cytokines in heart failure: pathogenetic mechanisms and potential treatment, Proc. Assoc. Am. Physicians, vol. 111, No. 5, pp. 423-428, Sep.-Oct. 1999.

Dinarello, C. A., The interleukin-1 family: 10 years of discovery, FASEB J., vol. 8, No. 15, pp. 1314-1325, Dec. 1994.

Dorr et al.; Effect of vagus nerve stimulation on serotonergic and noradrenergic transmission; J. Pharmacol. Exp. Ther.; 318(2); pp. 890-898; Aug. 2006.

Doshi et al., Evolving role of tissue factor and its pathway inhibitor, Crit. Care Med., vol. 30, suppl. 5, pp. S241-S250, May 2002.

Elenkov et al.; Stress, corticotropin-releasing hormone, glucocorticoids, and the immune / inflammatory response: acute and chronic effects; Ann. N.Y. Acad. Sci.; 876; pp. 1-13; Jun. 22, 1999.

Ellington et al., In vitro selection of RNA molecules that bind specific ligands, Nature, vol. 346, pp. 818-822, Aug. 30, 1990.

Ellrich et al.; Transcutaneous vagus nerve stimulation; Eur. Neurological Rev.; 6(4); pp. 254-256; 2011 (year of pub. sufficiently earlier than effective US filing date and any foreign priority date).

Engineer et al.; Directing neural plasticity to understand and treat tinnitus; Hear. Res.; 295; pp. 58-66; Jan. 2013.

Engineer et al.; Reversing pathological neural activity using targeted plasticity; Nature; 470(7332); pp. 101-104; Feb. 3, 2011 (Author Manuscript).

Esmon, The protein C pathway, Grit. Care Med., vol. 28, suppl. 9, pp. S44-S48, Sep. 2000.

Fields; New culprits in chronic pain; Scientific American; pp. 50-57; Nov. 2009.

Fleshner, M., et al., Thermogenic and corticosterone responses to intravenous cytokines (Il-1? and TNF-?) are attenuated by subdiaphragmatic vagotomy, J. Neuroimmunol., vol. 86(2), pp. 134-141, Jun. 1998.

Fox, D. A., Cytokine blockade as a new strategy to treat rheumatoid arthritis, Arch. Intern. Med., vol. 160, pp. 437-444, Feb. 28, 2000.

Fox, et al., Use of muscarinic agonists in the treatment of Sjorgren' syndrome, Clin. Immunol., vol. 101, No. 3; pp. 249-263, Dec. 2001.

Fujii et al.; Simvastatin regulates non-neuronal cholinergic activity in T lymphocytes via CD11a-mediated pathways; J. Neuroimmunol.; 179(1-2); pp. 101-107; Oct. 2006.

Gao et al.; Investigation of specificity of auricular acupuncture points in regulation of autonomic function in anesthetized rats; Autonomic Neurosc.; 138(1-2); pp. 50-56; Feb. 29, 2008.

Gattorno, M., et al., Tumor necrosis factor induced adhesion molecule serum concentrations in henoch-schoenlein purpura and pediatric systemic lupus erythematosus, J. Rheumatol., vol. 27, No. 9, pp. 2251-2255, Sep. 2000.

Gaykema, R. P., et al., Subdiaphragmatic vagotomy suppresses endotoxin-induced activation of hypothalamic corticotropin-releasing hormone neurons and ACTH secretion, Endocrinology, vol. 136, No. 10, pp. 4717-4720, Oct. 1995.

Ghelardini et al., S-(-)-ET 126: A potent and selective M1 antagonist in vitro and in vivo, Life Sciences, vol. 58, No. 12, pp. 991-1000, Feb. 1996.

Ghia, et al., The vagus nerve: a tonic inhibitory influence associated with inflammatory bowel disease in a murine model, Gastroenterology, vol. 131, No. 4, pp. 1122-1130, Oct. 2006.

Giebelen, et al., Stimulation of ?7 cholinergic receptors inhibits lipopolysaccharide-induced neutrophil recruitment by a tumor necrosis factor ?-independent mechanism, Shock, vol. 27, No. 4, pp. 443-447, Apr. 2007.

Goyal et al., Nature of the vagal inhibitory innervation to the lower esophageal sphincter, Journal of Clinical Investigation, vol. 55, pp. 1119-1126, May 1975.

Gracie, J. A., et al., A proinflammatory role for IL-18 in rheumatoid arthritis, J. Clin. Invest., vol. 104, No. 10, pp. 1393-1401, Nov. 1999.

(56) References Cited

OTHER PUBLICATIONS

Granert et al., Suppression of macrophage activation with CNI-1493 increases survival in infant rats with systemic haemophilus influenzae infection, Infection and Immunity, vol. 68, No. 9, pp. 5329-5334, Sep. 2000.
Green et al., Feedback technique for deep relaxation, Psycophysiology, vol. 6, No. 3, pp. 371-377, Nov. 1969.
Gregory et al., Neutrophil-kupffer-cell interaction in host defenses to systemic infections, Immunology Today, vol. 19, No. 11, pp. 507-510, Nov. 1998.
Groves et al.; Recordings from the rat locus coeruleus during acute vagal nerve stimulation in the anaesthetised rat; Neuroscience Letters; 379(3); pp. 174-179; May 13, 2005.
Guarente, Leonard, Ph. D.; Sirtuins, Aging, and Medicine; N Engl J Med ; vol. 364:pp. 2235-2244; Jun. 2011.
Guslandi, M., Nicotine treatment for ulcerative colitis, Br. J. Clin. Pharmacol., vol. 48(4), pp. 481-484, Oct. 1999.
Hansson, E.; Could chronic pain and spread of pain sensation be induced and maintained by glial activation?. Acta Physiologica, vol. 187, Issue 1-2; pp. 321R327, May/Jun. 2006.
Harrison's Principles of Internal Medicine, 13th Ed., pp. 511-515 and 1433-1435, Mar. 1994.
Hatton et al.; Vagal nerve stimulation: overview and implications for anesthesiologists; Int'l Anesthesia Research Society; vol. 103; No. 5; pp. 1241-1249; Nov. 2006.
Hirano, T., Cytokine suppresive agent improves survival rate in rats with acute pancreatitis of closed duodenal loop, J. Surg. Res., vol. 81, No. 2, pp. 224-229, Feb. 1999.
Hirao et al., The limits of specificity: an experimental analysis with RNA aptamers to MS2 coat protein variants, Mol. Divers., vol. 4, No. 2, pp. 75-89, 1999 (Accepted Jan. 13, 1999).
Hoffer et al.; Implantable electrical and mechanical interfaces with nerve and muscle; Annals of Biomedical Engineering; vol. 8; pp. 351-360; (year of pub. sufficiently earlier than effective US filing date and any foreign priority date) 1980.
Holladay et al., Neuronal nicotinic acetylcholine receptors as targets for drug discovery, Journal of Medicinal Chemistry, 40(26), pp. 4169-4194, Dec. 1997.
Hommes, D. W. et al., Anti- and Pro-inflammatory cytokines in the pathogenesis of tissue damage in Crohn's disease, Current Opinion in Clinical Nutrition and Metabolic Care, vol. 3(3), pp. 191-195, May 2000.
Hsu, et al., Analysis of efficiency of magnetic stimulation, IEEE Trans. Biomed. Eng., vol. 50(11), pp. 1276-1285, Nov. 2003.
Hsu, H. Y., et al., Cytokine release of peripheral blood monoculear cells in children with chronic hepatitis B virus infection, J. Pediatr. Gastroenterol., vol. 29, No. 5, pp. 540-545, Nov. 1999.
Hu, et al., The effect of norepinephrine on endotoxin-mediated macrophage activation, J. Neuroimmunol., vol. 31(1), pp. 35-42, Jan. 1991.
Huston et al.; Splenectomy inactivates the cholinergic antiinflammatory pathway during lethal endotoxemia and polymicrobial sepsis; J. Exp. Med. 2006; vol. 203, No. 7; pp. 1623-1628; Jun. 19, 2006.
Huston et al.; Transcutaneous vagus nerve stimulation reduces serum high mobility group box 1 levels and improves survival in murine sepsis; Crit. Care Med.; 35(12); pp. 2762-2768; Dec. 2007.
Hutchinson et al.; Proinflammatory cytokines oppose opioid induced acute and chronic analgesia; Brain Behav Immun.; vol. 22; No. 8; pp. 1178-1189; Nov. 2008.
Ilton et al., "Differential expression of neutrophil adhesion molecules during coronary artery surgery with cardiopulmonary bypass" Journal of Thoracic and Cardiovascular Surgery, Mosby-Year Book, inc., St. Louis, Mo, US, pp. 930-937, Nov. 1, 1999.
Jaeger et al., The structure of HIV-1 reverse transcriptase complexed with an RNA pseudoknot inhibitor, The EMBO Journal, 17(15), pp. 4535-4542, Aug. 1998.
Jander, S. et al., Interleukin-18 is induced in acute inflammatory demyelinating polymeuropathy, J. Neuroimmunol., vol. 114, pp. 253-258, Mar. 2001.

Joshi et al., Potent inhibition of human immunodeficiency virus type 1 replection by template analog reverse transcriptase , J. Virol., 76(13), pp. 6545-6557, Jul. 2002.
Kawahara et al.; SIRT6 links histone H3 lysine 9 deacetylation to NF-kappaB-dependent gene expression and organismal life span.; Cell. ; vol. 136; No. 1; pp. 62-74; Jan. 2009.
Kalishevskaya et al. "The character of vagotomy-and atropin-induced hypercoagulation," Sechenov Physiological Journal of the USSR, 65(3): pp. 398-404, Mar. 1979.
Kalishevskaya et al.; Nervous regulation of the fluid state of the blood; Usp. Fiziol. Nauk;,vol. 13; No. 2; pp. 93-122; Apr.-Jun. 1982.
Kanai, T. et al., Interleukin-18 and Crohn's disease, Digestion, vol. 63, suppl. 1, pp. 37-42, (year of pub. sufficiently earlier than effective US filing date and any foreign priority date) 2001.
Katagiri, M., et al., Increased cytokine production by gastric mucosa in patients with helicobacter pylon infection, J. Clin, Gastroenterol., vol. 25, Suppl. 1, pp. S211-S214, (year of pub. sufficiently earlier than effective US filing date and any foreign priority date) 1997.
Kawashima, et al., Extraneuronal cholinergic system in lymphocytes, Pharmacology & Therapeutics, vol. 86, pp. 29-48, Apr. 2000.
Kees et al; Via beta-adrenoceptors, stimulation of extrasplenic sympathetic nerve fibers inhibits lipopolysaccharide-induced TNF secretion in perfused rat spleen; J.Neuroimmunol.; 145(1-2); pp. 77-85; Dec. 2003.
Kensch et al., HIV-1 reverse transcriptase-pseudoknot RNA aptamer interaction has a binding affinity in the low picomolar range coupled with high specificity, J. Biol. Chem., 275(24), pp. 18271-18278, Jun. 16, 2000.
Khatun, S., et al., "Induction of hypercoagulability condition by chronic localized cold stress in rabbits," Thromb. and Haemost., 81(3): pp. 449-455, Mar. 1999.
Kimball, et al., Levamisole causes differential cytokine expression by elicited mouse peritoneal macrophases, Journal of Leukocyte Biology, vo. 52, No. 3, pp. 349-356, Sep. 1992 (abstract only).
Kimmings, A. N., et al., Systemic inflammatory response in acute cholangitis and after subsequent treatment, Eur. J. Surg., vol. 166, pp. 700-705, Sep. 2000.
Kirchner et al.; Left vagus nerve stimulation suppresses experimentally induced pain; Neurology; vol. 55; pp. 1167-1171; Oct. 2000.
Kokkula, R. et al., Successful treatment of collagen-induced arthritis in mice and rats by targeting extracellular high mobility group box chromosomal protein 1 activity, Arthritis Rheum., 48(7), pp. 2052-2058, Jul. 2003.
Koopman et al.; Pilot study of stimulation of the cholinergic anti-inflammatory pathway with an implantable vagus nerve stimulation device in patients with rheumatoid arthritis; Arth. Rheum.; 64(10 suppl.); pp. S195; Oct. 2012.
Krarup et al; Conduction studies in peripheral cat nerve using implanted electrodes: I. methods and findings in controls; Muscle & Nerve; vol. 11; pp. 922-932; Sep. 1988.
Kudrjashov, et al. "Reflex nature of the physiological anticoagulating system," Nature, vol. 196(4855): pp. 647-649; Nov. 17, 1962.
Kumins, N. H., et al., Partial hepatectomy reduces the endotoxin-induced peak circulating level of tumor necrosis factor in rats, Shock, vol. 5, No. 5, pp. 385-388, May 1996.
Kuznik, "Role of the vascular wall in the process of hemostatis," Usp Sovrem Biol., vol. 75(1): pp. 61-85, (year of pub. sufficiently earlier than effective US filing date and any foreign priority date) 1973.
Kuznik, et al., "Blood Coagulation in stimulation of the vagus nerve in cats," Biull. Eskp. Biol. Med., vol. 78 (7): pp. 7-9, (year of pub. sufficiently earlier than effective US filing date and any foreign priority date) 1974.
Kuznik, et al., "Heart as an efferent regulator of the process of blood coagulation and fibrinolysis," Kardiologiia, vol. 13(3): pp. 10-17, (year of pub. sufficiently earlier than effective US filing date and any foreign priority date) 1973.
Kuznik, et al., "Role of the heart and vessels in regulating blood coagulation and fibrinolysis," Kagdiologiia, vol. 13 (4): pp. 145-154, (year of pub. sufficiently earlier than effective US filing date and any foreign priority date) 1973.

(56) References Cited

OTHER PUBLICATIONS

Kuznik, et al., "Secretion of blood coagulation factors into saliva under conditions of hypo-and hypercoagulation," Voprosy Meditsinskoi Khimii, vol. 19(1): pp. 54-57; (year of pub. sufficiently earlier than effective US filing date and any foreign priority date) 1973.
Kuznik, et al., "The dynamics of procoagulatible and fibrinolytic activities during electrical stimulation of peripheral nerves," Sechenov Physiological Journal of the USSR, vol. 65; No. 3: pp. 414-420, Mar. 1979.
Kuznik, et al., "The role of the vascular wall in the mechanism of control of blood coagulation and fibrinolysis on stimulation of the vagus nerve," Cor Vasa, vol. 17(2): pp. 151-158, (year of pub. sufficiently earlier than effective US filing date and any foreign priority date) 1975.
Lang, et al., "Neurogienic control of cerebral blood flow," Experimental Neurology, 43(1): pp. 143-161, Apr. 1974.
Lee, H. G., et al., Peritoneal lavage fluids stimulate NIH3T3 fibroblast proliferation and contain increased tumour necrosis factor and IL6 in experimental silica-induced rat peritonitis, Clin. Exp. Immunol., vol. 100, pp. 139-144, Apr. 1995.
LeNovere, N. et al., Molecular evolution of the nicotinic acetylcholine receptor: an example of multigene family in excitable cells, J. Mol. Evol., 40, pp. 155-172, Feb. 1995.
Leonard, S. et al., Neuronal nicotinic receptors: from structure to function, Nicotine & Tobacco Res. 3:203-223, Aug. 2001.
Lips et al.; Coexpression and spatial association of nicotinic acetylcholine receptor subunits alpha7 and alpha10 in rat sympathetic neurons; J.Mol.Neurosci.; 30; pp. 15-16; (year of pub. sufficiently earlier than effective US filing date and any foreign priority date) 2006.
Lipton, J. M. et al.; Anti-inflammatory actions of the neuroimmunomodulator ?—MSH, Immunol. Today, vol. 18, pp. 140-145, Mar. 1997.
Loeb et al.; Cuff electrodes for chronic stimulation and recording of peripheral nerve activity; Journal of Neuroscience Methods; vol. 64; pp. 95-103; Jan. 1996.
Madretsma, G. S., et al., Nicotine inhibits the in vitro production of interleukin 2 and tumour necrosis factor-alpha by human monocuclear cells, Immunopharmacology, vol. 35, No. 1, pp. 47-51, Oct. 1996.
Martindale: The Extra Pharmacopoeia; 28th Ed. London; The pharmaceutical press; pp. 446-485; (year of pub. sufficiently earlier than effective US filing date and any foreign priority date) 1982.
Martiney et al., Prevention and treatment of experimental autoimmune encephalomyelitis by CNI-1493, a macrophage-deactivating agent, Journal of Immunology, vol. 160, No. 11, pp. 5588-5595, Jun. 1, 1998.
McGuinness, P. H., et al., Increases in intrahepatic CD68 positive cells, MAC387 positive cells, and proinflammatory cytokines (particulary interleukin 18) in chronic hepatitis C infection, Gut, vol. 46, pp. 260-269, (year of pub. sufficiently earlier than effective US filing date and any foreign priority date) 2000.
Miguel-Hidalgo, J.J.; The role of glial cells in drug abuse; Current Drug Abuse Reviews; vol. 2; No. 1; pp. 76-82; Jan. 2009.
Milligan et al.; Pathological and protective roles of glia in chronic pain; Nat Rev Neurosci.; vol. 10; No. 1; pp. 23-26; Jan. 2009.
Minnich et al.; Anti-cytokine and anti-inflammatory therapies for the treatment of severe sepsis: progress and pitfalls; Proceedings of the Nutrition Society; vol. 63(3); pp. 437-441; (year of pub. sufficiently earlier than effective US filing date and any foreign priority date) 2004.
Mishchenko, et al., "Coagulation of the blood and fibrinolysos in dogs during vagal stimulation," Sechenov Physiological Journal of the Ussr, vol. 61(1): pp. 101-107, (year of pub. sufficiently earlier than effective US filing date and any foreign priority date) 1975.
Mishchenko, "The role of specific adreno- and choline-receptors of the vascular wall in the regulation of blood coagulation in the stimulation of the vagus nerve," Biull. Eskp. Biol. Med., vol. 78(8): pp. 19-22, (year of pub. sufficiently earlier than effective US filing date and any foreign priority date) 1974.
Molina et al., CNI-1493 attenuates hemodynamic and pro-inflammatory responses to LPS, Shock, vol. 10, No. 5, pp. 329-334, Nov. 1998.
Nadol et al., "Surgery of the Ear and Temporal Bone," Lippinkott Williams & Wilkins, 2nd Ed., 2005, (Publication date: Sep. 21, 2004), p. 580.
Nagashima et al., Thrombin-activatable fibrinolysis inhibitor (TAFI) deficiency is compatible with murine life, J. Clin. Invest., 109, pp. 101-110, Jan. 2002.
Nathan, C. F., Secretory products of macrophages, J. Clin. Invest., vol. 79 (2), pp. 319-326, Feb. 1987.
Navai Kar et al.; Irbesartan, an angiotensin type 1 receptor inhibitor, regulates markers of inflammation in patients with premature atherosclerosis; Journal of the American College of Cardiology; vol. 37; No. 2; pp. 440-444; Feb. 2001.
Navzer et al.; Reversing pathological neural activity using targeted plasticity; Nature; 470(7332); pp. 101-104; Feb. 3, 2011.
Neuhaus et al.; P300 is enhanced in responders to vagus nerve stimulation for treatment of major depressive disorder; J. Affect. Disord.; 100(1-3); pp. 123-128; Jun. 2007.
Noguchi et al., Increases in Gastric acidity in response to electroacupuncture stimulation of hindlimb of anesthetized rats, Jpn. J. Physiol., 46(1), pp. 53-58, Feb. 1996.
Norton, Can ultrasound be used to stimulate nerve tissue, BioMedical Engineering OnLine, 2(1), pp. 6, Mar. 4, 2003.
Olofsson et al.; Rethinking inflammation: neural circuits in the regulation of immunity; Immunological Reviews; 248(1); pp. 188-204; Jul. 2012.
Oshinsky et al.; Non-invasive vagus nerve stimulation as treatment for trigeminal allodynia; Pain; 155(5); pp. 1037-1042; May 2014.
Palmblad et al., Dynamics of early synovial cytokine expression in rodent collagen-induced arthritis: a thereapeutic study unding a macrophage-deactivation compound, American Journal of Pathology, vol. 158, No. 2, pp. 491-500, Feb. 2, 2001.
Pateyuk, et al.,"Treatment of Botkin's disease with heparin," Klin. Med., vol. 51(3): pp. 113-117, Mar. 1973.
Pavlov et al; Controlling inflammation: the cholinergic anti-inflammatory pathway; Biochem. Soc. Trans.; 34(Pt 6); pp. 1037-1040; Dec. 2006.
Payne, J. B. et al., Nicotine effects on PGE2 and IL-1 beta release by LPS-treated human monocytes, J. Perio. Res., vol. 31, No. 2, pp. 99-104, Feb. 1996.
Peuker; The nerve supply of the human auricle; Clin. Anat.; 15(1); pp. 35-37; Jan. 2002.
Prystowsky, J. B. et al., Interleukin-1 mediates guinea pig gallbladder inflammation in vivo, J. Surg. Res., vol. 71, No. 2, pp. 123-126, Aug. 1997.
Pulkki, K. J., Cytokines and cardiomyocyte death, Ann. Med., vol. 29(4), pp. 339-343, Aug. 1997.
Pullan, R. D., et al., Transdermal nicotine for active ulceratiive colitis, N. Engl. J. Med., vol. 330, No. 12, pp. 811-815, Mar. 24, 1994.
Pulvirenti et al; Drug dependence as a disorder of neural plasticity:focus on dopamine and glutamate; Rev Neurosci.; vol. 12; No. 2; pp. 141-158; Apr./Jun. 2001.
Rahman et al.; Mammalian Sirt 1: Insights on its biological functions; Cell Communications and Signaling; vol. 9; No. 11; pp. 1-8; May 2011.
Rayner, S. A. et al., Local bioactive tumour necrosis factor (TNF) in corneal allotransplantation, Clin. Exp. Immunol., vol. 122, pp. 109-116, Oct. 2000.
Reale et al.; Treatment with an acetylcholinesterase inhibitor in alzheimer patients modulates the expression and production of the pro-inflammatory and anti-inflammatory cytokines; J. Neuroimmunology; 148(1-2); pp. 162-171; Mar. 2004.
Rinner et al.; Rat lymphocytes produce and secrete acetylcholine in dependence of differentiation and activation; J.Neuroimmunol.; 81(1-2); pp. 31-37; Jan. 1998.
Robinson et al.; Studies with the Electrocardiograph on the Action of the Vagus Nerve on the Human Heart; J Exp Med; 14(3):217-234; Sep. 1911.

(56) References Cited

OTHER PUBLICATIONS

Romanovsky, A. A., et al., The vagus nerve in the thermoregulatory response to systemic inflammation, Am. J. Physiol., vol. 273, No. 1 (part 2), pp. R407-R413, Jul. 1, 1997.
Saghizadeh et al.; The expression of TNF? by human muscle; J. Clin. Invest.; vol. 97; No. 4; pp. 1111-1116; Feb. 15, 1996.
Saindon et al.; Effect of cervical vagotomy on sympathetic nerve responses to peripheral interleukin-1beta; Auton.Neuroscience Basic and Clinical; 87; pp. 243-248; Mar. 23, 2001.
Saito, Involvement of muscarinic M1 receptor in the central pathway of the serotonin-induced bezold-jarisch reflex in rats, J. Autonomic Nervous System, vol. 49, pp. 61-68, Sep. 1994.
Sandborn, W. J., et al., Transdermal nicotine for mildly to moderately active ulcerative colitis, Ann. Intern. Med, vol. 126, No. 5, pp. 364-371, Mar. 1, 1997.
Sato, E., et al., Acetylcholine stimulates alveolar macrophages to release inflammatory cell chemotactic activity, Am. J. Physiol., vol. 274, pp. L970-L979, Jun. 1998.
Sato, K.Z., et al., Diversity of mRNA expression for muscarinic acetylcholine receptor subtypes and neuronal nicotinic acetylcholine receptor subunits in human mononuclear leukosytes and leukemic cell lines, Neuroscience Letters, vol. 266, pp. 17-20, Apr. 30, 1999.
Scheinman, R. I., et al., Role of transcriptional activation of I?B? in mediation of immunosuppression by glucocorticoids, Science, vol. 270, No. 5234, pp. 283-286, Oct. 13, 1995.
Schneider et al., High-affinity ssDNA inhibitors of the review transcriptase of type 1 human immunodeficiency virus, Biochemistry, 34(29), pp. 9599-9610, (year of pub. sufficiently earlier than effective US filing date and any foreign priority date) 1995.
Shafer, Genotypic testing for human immunodeficiency virus type 1 drug resistance, Clinical Microbiology Reviews, vol. 15, pp. 247-277, Apr. 2002.
Shapiro et al.; Prospective, randomised trial of two doses of rFVIIa (NovoSeven) in haemophilia patients with inhibitors undergoing surgery; Thromb Haemost; vol. 80(5); pp. 773-778; Nov. 1998.
Sher, M. E., et al., The influence of cigarette smoking on cytokine levels in patients with inflammatory bowel disease, Inflamm. Bowel Dis., vol. 5, No. 2, pp. 73-78, May 1999.
Shi et al.; Effects of efferent vagus nerve excitation on inflammatory response in heart tissue in rats with endotoxemia; vol. 15, No. 1; pp. 26-28; Jan. 2003 (Eng. Abstract).
Snyder et al., Correction of hemophilia B in canine and murine models using recombinant adeno-associated viral vectors; Nature Medicine, 5(1); pp. 64-70, Jan. 1999.
Sokratov, et al. "The role of choline and adrenegic structures in regulation of renal excretion of hemocoagulating compounds into the urine," Sechenov Physiological Journal of the USSR, vol. 63(12): pp. 1728-1732, (year of pub. sufficiently earlier than effective US filing date and any foreign priority date) 1977.
Stalcup et al., Endothelial cell functions in the hemodynamic responses to stress, Annals of the New York Academy of Sciences, vol. 401, pp. 117-131, Dec. 1982.
Steinlein, New functions for nicotine acetylcholine receptors?, Behavioural Brain Res., vol. 95, pp. 31-35, (year of pub. sufficiently earlier than effective US filing date and any foreign priority date) 1998.
Sternberg, E. M., Perspectives series: cytokines and the brain 'neural-immune interactions in health and disease,' J. Clin. Invest., vol. 100, No. 22, pp. 2641-2647, Dec. 1997.
Stevens et al.; The anti-inflammatory effect of some immunosuppressive agents; J. Path.; 97(2); pp. 367-373 (year of pub. sufficiently earlier than effective US filing date and any foreign priority date); 1969.
Strojnik et al.; Treatment of drop foot using and implantable peroneal underknee stimulator; Scand. J. Rehab. Med.; vol. 19(1); pp. 37R43; (year of pub. sufficiently earlier than effective US filing date and any foreign priority date) 1987.
Sugano et al., Nicotine inhibits the production of inflammatory mediators in U937 cells through modulation of nuclear factor-kappaβ, activation, Biochemical and Biophysical Research Communications, vol. 252, No. 1, pp. 25-28, Nov. 9, 1998.
Suter et al.; Do glial cells control pain?; Neuron Glia Biol.; vol. 3; No. 3; pp. 255-268; Aug. 2007.
Swick et al.; Locus coeruleus neuronal activity in awake monkeys: relationship to auditory P300-like potentials and spontaneous EEG. Exp. Brain Res.; 101(1); pp. 86-92; Sep. 1994.
Sykes, et al., An investigation into the effect and mechanisms of action of nicotine in inflammatory bowel disease, Inflamm. Res., vol. 49, pp. 311-319, Jul. 2000.
Takeuchi et al., A comparision between chinese blended medicine "Shoseiryuto" tranilast and ketotifen on the anit-allergic action in the guinea pigs, Allergy, vol. 34, No. 6, pp. 387-393, Jun. 1985 (eng. abstract).
Tekdemir et al.; A clinico-anatomic study of the auricular branch of the vagus nerve and arnold's ear-cough reflex; Surg. Radiol. Anat.; 20(4); pp. 253-257; Mar. 1998.
Toyabe, et al., Identification of nicotinic acetylcholine receptors on lymphocytes in the periphery as well as thymus in mice, Immunology, vol. 92(2), pp. 201-205, Oct. 1997.
Tracey et al., Mind over immunity, Faseb Journal, vol. 15, No. 9, pp. 1575-1576, Jul. 2001.
Tracey, K. J. et al., Anti-cachectin/TNF monoclonal antibodies prevent septic shock during lethal bacteraemia; Nature, 330: pp. 662-664, Dec. 23, 1987.
Tracey, K. J. et al., Physiology and immunology of the cholinergic antiinflammatory pathway; J Clin Invest.; vol. 117: No. 2; pp. 289-296; Feb. 2007.
Tracey, K. J.; Reflex control of immunity; Nat Rev Immunol; 9(6); pp. 418-428; Jun. 2009.
Tracey, K. J. et al., Shock and tissue injury induced by recombinant human cachectin, Science, vol. 234, pp. 470-474, Oct. 24, 1986.
Tracey, K.J., The inflammatory reflex, Nature, vol. 420, pp. 853-859, Dec. 19-26, 2002.
Tsutsui, H., et al., Pathophysiolocical roles of interleukin-18 in inflammatory liver diseases; Immunol. Rev., 174:192-209, Apr. 2000.
Tuerk et al., RNA pseudoknots that inhibit human immunodeficiency virus type 1 reverse transcriptase; Proc. Natl. Acad. Sci. USA, 89, pp. 6988-6992, Aug. 1992.
Tuerk et al., Systematic evolution of ligands by exponential enrichment: RNA ligands to bacteriophage T4 DNA polymerase; Science, 249(4968), pp. 505-510, Aug. 3, 1990.
Van Dijk, A. P., et al., Transdermal nictotine inhibits interleukin 2 synthesis by mononuclear cells derived from healthy volunteers, Eur. J. Clin. Invest, vol. 28, pp. 664-671, Aug. 1998.
Van Der Horst et al.; Stressing the role of FoxO proteins in lifespan and disease; Nat Rev Mol Cell Biol.; vol. 8; No. 6; pp. 440-450; Jun. 2007.
Vanhoutte, et al., Muscarinic and beta-adrenergic prejunctional modulation of adrenergic neurotransmission in the blood vessel wall, Gen Pharmac., vol. 14, pp. 35-37, (year of pub. sufficiently earlier than effective US filing date and any foreign priority date) 1983.
vanWesterloo, et al., The cholinergic anti-inflammatory pathway regulates the host response during septic peritonitis, The Journal of Infectious Diseases, vol. 191, pp. 2138-2148, Jun. 15, 2005.
Ventureyra, Transcutaneous vagus nerve stimulation for partial onset seizure therapy, Child's Nerv Syst, vol. 16 (2), pp. 101-102, (year of pub. sufficiently earlier than effective US filing date and any foreign priority date) 2000.
Vijayaraghavan, S.; Glial-neuronal interactions-implications for plasticity anddrug addictionl AAPS J.; vol. 11; No. 1; pp. 123-132; Mar. 2009.
Villa et al., Protection against lethal polymicrobial sepsis by CNI-1493, an inhibitor of pro-inflammatory cytokine synthesis, Journal of Endotoxin Research, vol. 4, No. 3, pp. 197-204, Jun. 1997.
Von Känel, et al., Effects of non-specific ?-adrenergic stimulation and blockade on blood coagulation in hypertension, J. Appl. Physiol., vol. 94, pp. 1455-1459, Apr. 2003.
Von Känel, et al., Effects of sympathetic activation by adrenergic infusions on hemostasis in vivo, Eur. J. Haematol., vol. 65: pp. 357-369, Dec. 2000.

(56) References Cited

OTHER PUBLICATIONS

Walland et al., Compensation of muscarinic brochial effects of talsaclidine by concomitant sympathetic activation in guinea pigs; European Journal of Pharmacology, vol. 330(2-3), pp. 213-219, Jul. 9, 1997.

Wang et al; Nicotinic acetylcholine receptor alpha7 subunit is an essential regulator of inflammation; Nature; 421; 384-388; Jan. 23, 2003.

Wang, H., et al., HMG-1 as a late mediator of endotoxin lethality in mice, Science, vol. 285, pp. 248-251, Jul. 9, 1999.

Waserman, S. et al., TNF-? dysregulation in asthma: relationship to ongoing corticosteroid therapy, Can. Respir. J., vol. 7, No. 3, pp. 229-237, May-Jun. 2000.

Watanabe, H. et al., The significance of tumor necrosis factor (TNF) levels for rejection of joint allograft, J. Reconstr. Microsurg., vol. 13, No. 3, pp. 193-197, Apr. 1997.

Wathey, J.C. et al., Numerical reconstruction of the quantal event at nicotinic synapses; Biophys. J., vol. 27: pp. 145-164, Jul. 1979.

Watkins, L.R. et al., Blockade of interleukin-1 induced hyperthermia by subdiaphragmatic vagotomy: evidence for vagal mediation of immune-brain communication, Neurosci. Lett., vol. 183(1-2), pp. 27-31, Jan. 1995.

Watkins, L.R. et al., Implications of immune-to-brain communication for sickness and pain, Proc. Natl. Acad. Sci. U.S.A., vol. 96(14), pp. 7710-7713, Jul. 6, 1999.

Webster's Dictionary, definition of "intrathecal", online version accessed Apr. 21, 2009.

Weiner, et al., "Inflammation and therapeutic vaccination in CNS diseases," Nature., vol. 420(6917): pp. 879-884, Dec. 19-26, 2002.

Westerheide et al.; Stress-inducible regulation of heat shock factor 1 by the deacetylase SIRT1.; Science; Vo. 323; No. 5717; pp. 1063-1066; Feb. 2009.

Whaley, K. et al., C2 synthesis by human monocytes is modulated by a nicotinic cholinergic receptor, Nature, vol. 293, pp. 580-582, Oct. 15, 1981.

Woiciechowsky, C. et al., Sympathetic activation triggers systemic interleukin-10 release in immunodepression induced by brain injury, Nature Med., vol. 4, No. 7, pp. 808-813, Jul. 1998.

Yeh, S.S. et al., Geriatric cachexia: the role of cytokines, Am. J. Clin. Nutr., vol. 70(2), pp. 183-197, Aug. 1999.

Yu et al.; Low-level transcutaneous electrical stimulation of the auricular branch of the vagus nerve: a non-invasive approach to treat the initial phase of atrial fibrillation; Heart Rhythm; 10(3); pp. 428-435; Mar. 2013.

Zamotrinsky et al.; Vagal neurostimulation in patients with coronary artery disease; Auton. Neurosci.; 88(1-2); pp. 109-116; Apr. 2001.

Zhang et al., Tumor necrosis factor, The Cytokine Handbook, 3rd ed., Ed. Thompson, Academic Press, pp. 517-548, Jul. 1, 1998.

Zhang et al.; Roles of SIRT1 in the acute and restorative phases following induction of inflammation.; J Biol Chem.; vol. 285; No. 53; pp. 41391-41401; Dec. 2010.

Zhang et al.; Chronic vagus nerve stimulation improves autonomic control and attenuates systemic inflammation and heart failure progression in a canine high-rate pacing model; Circulation Heart Fail.; 2; pp. 692-699; Nov. 2009.

Zhao et al.; Transcutaneous auricular vagus stimulation protects endotoxemic rat from lipopolysaccharide-induced inflammation; Evid. Based Complement Alternat. Med.; vol. 2012; Article ID 627023; 10 pages; Dec. 29, 2012.

Levine et al.; U.S. Appl. No. 14/782,715 entitled "Closed-loop vagus nerve stimulation," filed Oct. 6, 2015.

Levine et al.; U.S. Appl. No. 14/922,022 entitled "Systems and methods for stimulating and/or monitoring loci in the brain to treat inflammation and to enhance vagus nerve stimulation," filed Oct. 23, 2015.

Levine et al.; U.S. Appl. No. 14/968,702 entitled "Extremely low duty-cycle activation of the cholinergic anti-inflammatory pathway to treat chronic inflammation," filed Dec. 14, 2015.

METHODS AND SYSTEMS FOR REDUCING INFLAMMATION BY NEUROMODULATION AND ADMINISTRATION OF AN ANTI-INFLAMMATORY DRUG

CROSS-REFERENCE TO RELATED APPLICATIONS

This patent application is a continuation-in-part of U.S. patent application Ser. No. 12/415,671, filed Mar. 31, 2009, titled "METHODS AND SYSTEMS FOR REDUCING INFLAMMATION BY NEUROMODULATION OF T-CELL ACTIVITY," now U.S. Pat. No. 9,211,409, which claims the benefit of U.S. Provisional Patent Application No. 61/072,603, titled "DEVICES AND METHODS FOR NEUROMODULATOIN OF T-CELL ACTIVITY," filed Mar. 31, 2008, each of which is herein incorporated by reference in its entirety.

STATEMENT REGARDING FEDERALLY SPONSORED RESEARCH

This invention was made with government support under grant(s) R01 GM057226 and R01 GM062508 awarded by the National Institutes of Health. The government has certain rights in the invention.

BACKGROUND OF THE INVENTION

Cytokine production is counter-regulated by evolutionarily ancient mechanisms. The cholinergic anti-inflammatory pathway is an anti-inflammatory neural mechanism for suppressing cytokine release by the immune system. It functions by signals carried via the vagus nerve that suppress cytokine release through a molecular mechanism that requires the alpha7 nicotinic acetylcholine receptor subunit (alpha7 nAChR). Direct electrical (or mechanical) stimulation of the vagus nerve attenuates cytokine release and prevents tissue injury in experimental animals with cytokine mediated diseases, including endotoxemia, hemorrhagic shock, ischemia-reperfusion, sepsis, colitis, and arthritis. The functional integrity of this pathway is critical for modulating the innate immune response to endotoxins, because eliminating the function, by either cutting the vagus nerve, or removing the alpha7 nAChR gene, renders animals exquisitely sensitive to otherwise innocuous quantities of endotoxins.

Early observations into the anatomic and functional basis of the cholinergic anti-inflammatory pathway implicate neural input to spleen as essential for vagus nerve mediated decreases of TNF during endotoxemia. Electrical stimulation of the vagus nerve in the neck attenuates TNF mRNA and protein levels in spleen, a major source of TNF in endotoxemia. Surgical ablation of the vagus nerve branches to the celiac ganglion disrupts the TNF-suppressive activity of cervical vagus nerve stimulation. Innervation to the spleen is provided by the splenic nerve, a catecholaminergic nerve that originates in the celiac ganglion. Since the cholinergic antiiflammatory pathway requires alpha7 nAChR signals, we examined how signals originating in vagus nerve reach the TNF-producing cells in spleen. Here we show that the splenic nerve is required for vagus nerve stimulation control of TNF production. Splenic nerve endings culminate adjacent to TNF producing macrophages and adjacent to T cells. Surprisingly, T cells are required for the functional integrity of the neural signals that inhibit TNF in spleen. As a result, we suggest methods and devices for treatment of disorders by stimulation of the inflammatory reflex (including the vagus nerve) in combination with modulation of T-Cells. Modulation of T-Cells, which may (in part) mediate the inflammatory reflex may help in further controlling the inflammatory reflex.

This application is related to U.S. Pat. No. 6,610,713; U.S. patent application Ser. No. 10/990,938, titled "Inhibition of Inflammatory Cytokine Production by Cholinergic Agonists and Vagus Nerve Stimulation," filed Nov. 17, 2004; and U.S. patent application Ser. No. 11/318,075, titled "Treating Inflammatory Disorders by Electrical Vagus Nerve Stimulation," filed Dec. 23, 2005. Each of these patents and pending applications is herein incorporated by reference in its entirety.

SUMMARY OF THE INVENTION

Described herein are devices, systems and method of treating an inflammatory response, including a method of treating a T-cell mediated disease. For example, described herein is a method of treating an inflammatory response comprising: stimulating a subject's inflammatory reflex to inhibit the immune response; and administering a T-cell modifying agent.

Inflammatory responses to pathogens and tissue injury are precisely controlled to prevent excessive tissue injury. Signals in the cholinergic anti-inflammatory pathway, in which efferent vagus nerve signals inhibit cytokine production, require the alpha7 nicotinic acetylcholine receptor subunit (alpha7 nAChR), which binds acetylcholine and suppresses the nuclear translocation of NFkB. Despite the importance of this pathway in controlling cytokine production, the cellular target of the neural signals during endotoxemia was previously unknown. Here, immunohistochemical staining of spleen during endotoxemia revealed that splenic nerve endings terminate adjacent to discrete macrophage populations producing TNF, and next to T cells that produce acetylcholine. Application of either vagus nerve stimulation, or administration of nicotine, an alpha7 agonist, significantly attenuates TNF production by the subpopulation TNF-producing splenic macrophages. Surprisingly, however, vagus nerve stimulation of nude mice failed to inhibit TNF production. Administration of nicotine to nude mice did significantly inhibit TNF production, indicating that T cells are essential for the neural, but not molecular activation of the cholinergic anti-inflammatory pathway. Together these results indicate that T cells are required for regulation of TNF by vagus nerve signals to spleen, and identify a previously unknown role for T cells in the function of the cholinergic anti-inflammatory pathway.

In the methods, systems and devices described herein, the stimulation of the subject's inflammatory reflex may be electrical stimulation, mechanical stimulation, or any other appropriate method of stimulation. In particular, long-term stimulation methods (e.g., non-contact, non-desensitizing methods) may be preferred.

Any appropriate T-cell modifying agent may be used with the methods, systems and devices described herein. For example, the T-Cell modifying agent may be selected from the group consisting of: glucocorticoids, antibody agents, peptide agents, drugs, and pro-drugs.

The step of stimulating the subject's inflammatory reflex may comprise stimulating the subject's vagus nerve (and/or afferent or efferents of the vagus nerve). In some variations the step of stimulating the subject's inflammatory reflex comprises stimulating one or more of: the vagus nerve, the splenic nerve, the hepatic nerve and the trigeminal nerve, and their afferents and efferents.

The step of administering a T-cell modifying agent may comprises systemic administration of the T-cell modifying agent, or local administration of the T-cell modifying agent (e.g., to the spleen or general splenic region). A T-cell modifying anent may be administered at any time in the method, for example, before, during and/or after stimulating the subject's inflammatory reflex.

In some variations, the step of stimulating the inflammatory reflex comprises repeatedly and periodically stimulating the subject's inflammatory reflex. For example, a subject's vagus nerve may be stimulated every 4 hours, every 8 hours, every 12 hours, every 24 hours, every 2 days, etc. The method may also included additional administration of T-cell modifying agents. For example, a T-cell modifying agent may be applied at various times during the treatment method.

Also described herein are methods of treating T cell-mediated diseases comprising the steps of identifying a patient suffering from a condition mediated by T-cell cells, stimulating the subject's inflammatory reflex, and administering a T-cell modifying agent. The T-cell mediated disease may be selected from the group consisting of: transplant rejection, rheumatoid arthritis, Psoriasis, or multiple sclerosis.

INCORPORATION BY REFERENCE

All publications and patent applications mentioned in this specification are herein incorporated by reference in their entirety to the same extent as if each individual publication or patent application was specifically and individually indicated to be incorporated by reference.

DETAILED DESCRIPTION OF THE INVENTION

Figure 1:
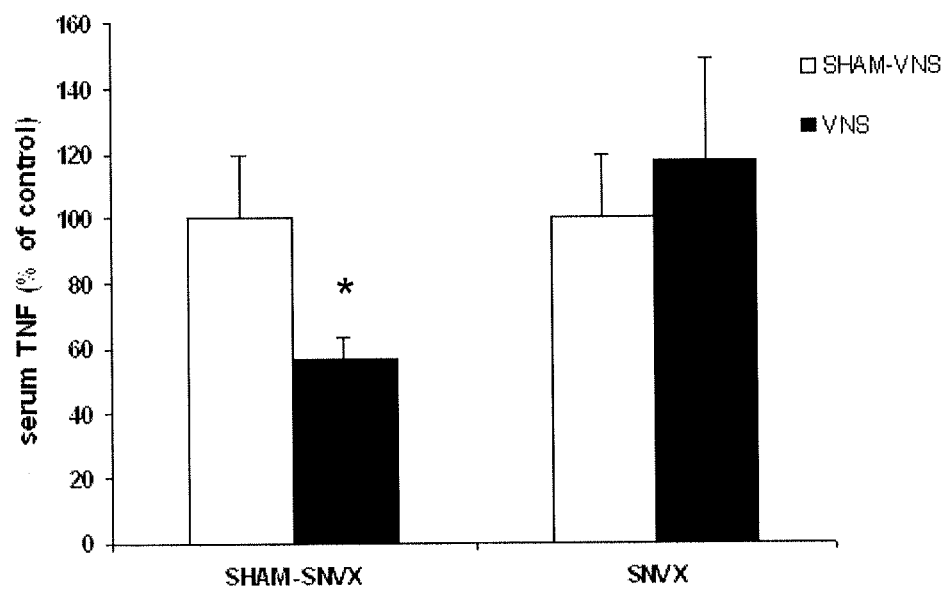
FIG. 1 shows the loss of inhibition the inflammatory reflex (measured by serum TNF) after cutting the splenic nerve (right side) compared to control (sham, left side). Inhibition of the inflammatory reflex is caused by VNS (vagus nerve stimulation), as previously described.
Figures 2A, 2B, 2C, 2D:
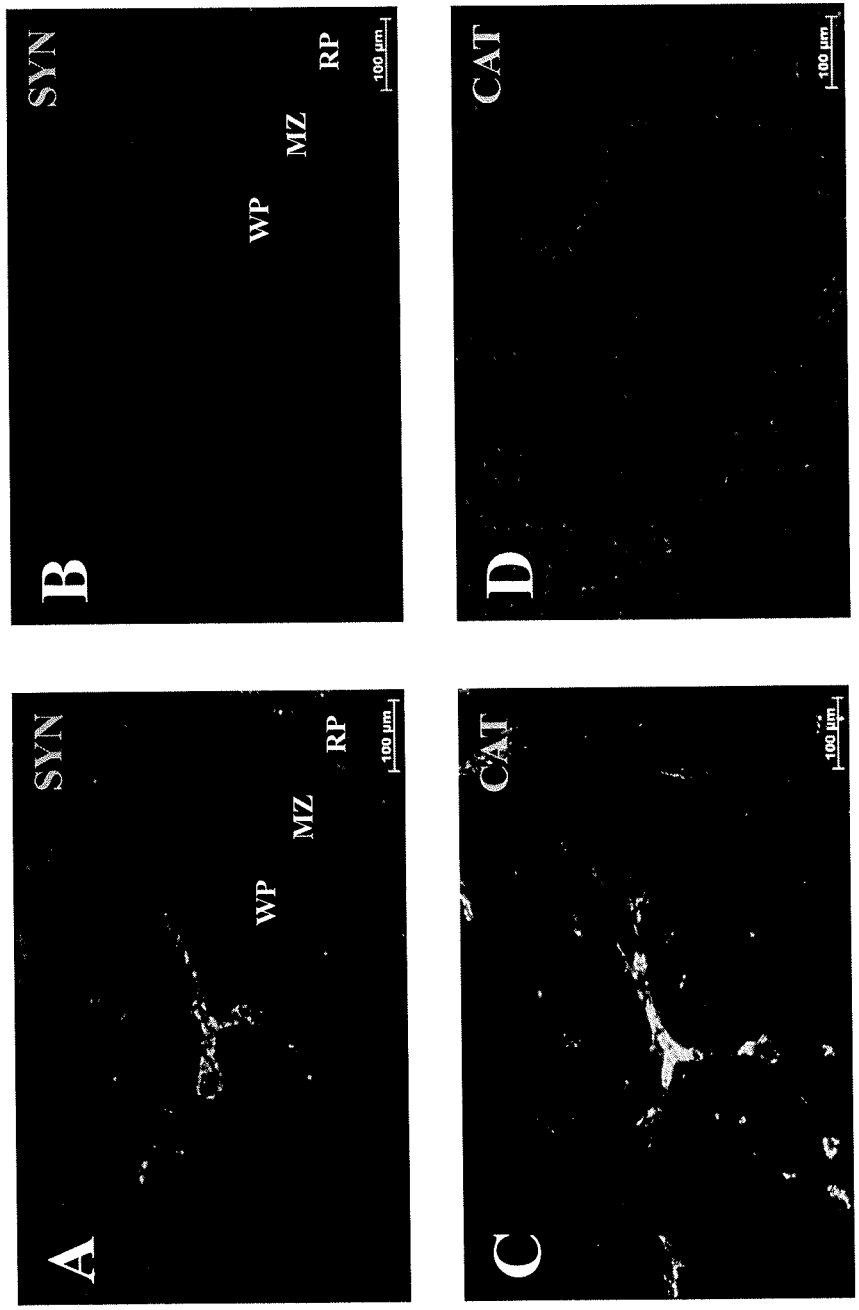
FIGS. 2A and 2B shows immunohistochmeical staining for synaptophysin (SYN) either before (FIG. 2A) or after (FIG. 2B) cutting the splenic nerve.
FIGS. 2C and 2D shows immunohistochemical staining for catecholaminergic neurons (CAT) before (FIG. 2C) or after (FIG. 2D) cutting the splenic nerve.
Figures 3A, 3B, 3C, 3D:
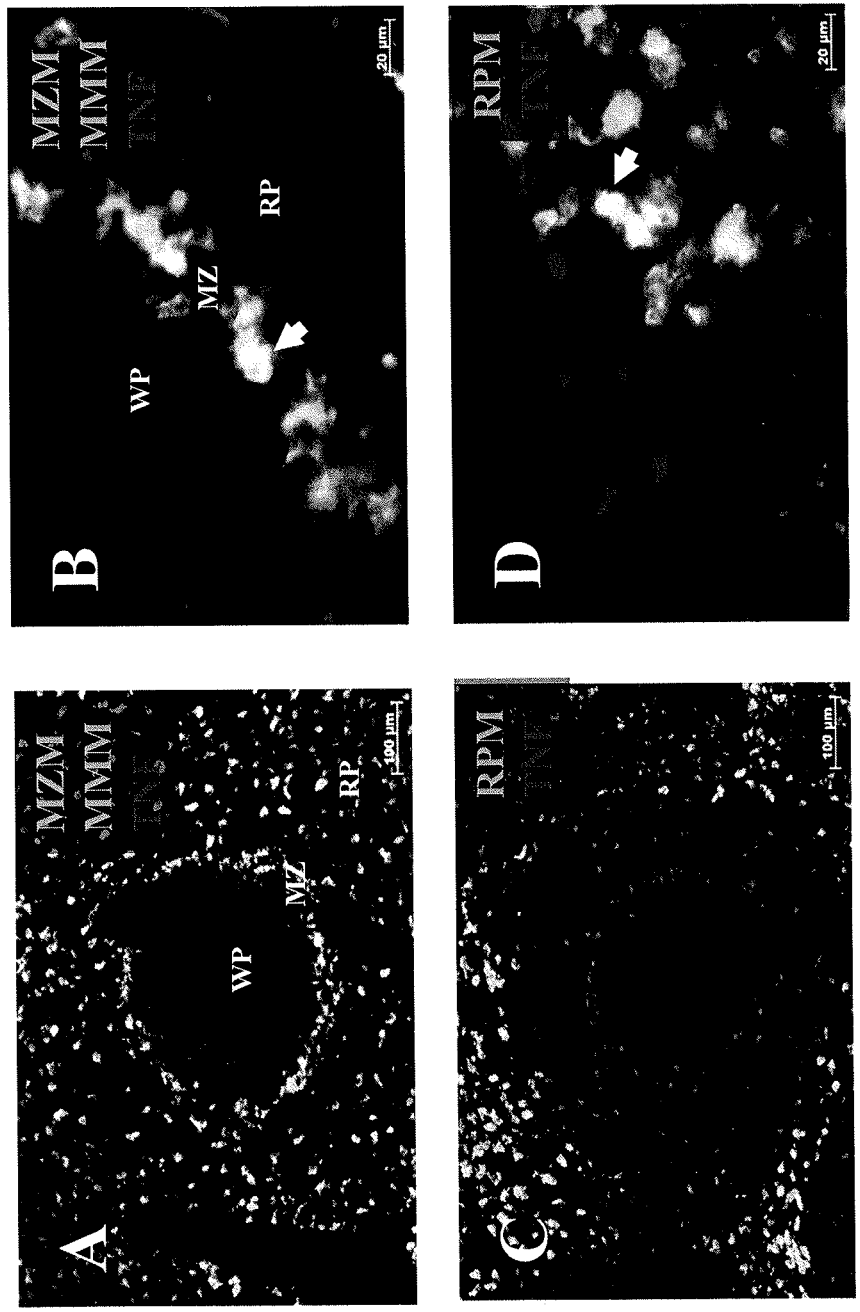
FIGS. 3A-3D show immunohistochemical staining with specific markers of macrophage subpopulations and TNF. MZM (marginal zone macrophages) and MMM (marginal metallophilic macrophages) and red pulp macrophages are indicated from this splenic section. TNF staining overlapped with marginal zone and the red pulp regions.
Figures 4A, 4B, 4C, 4D:
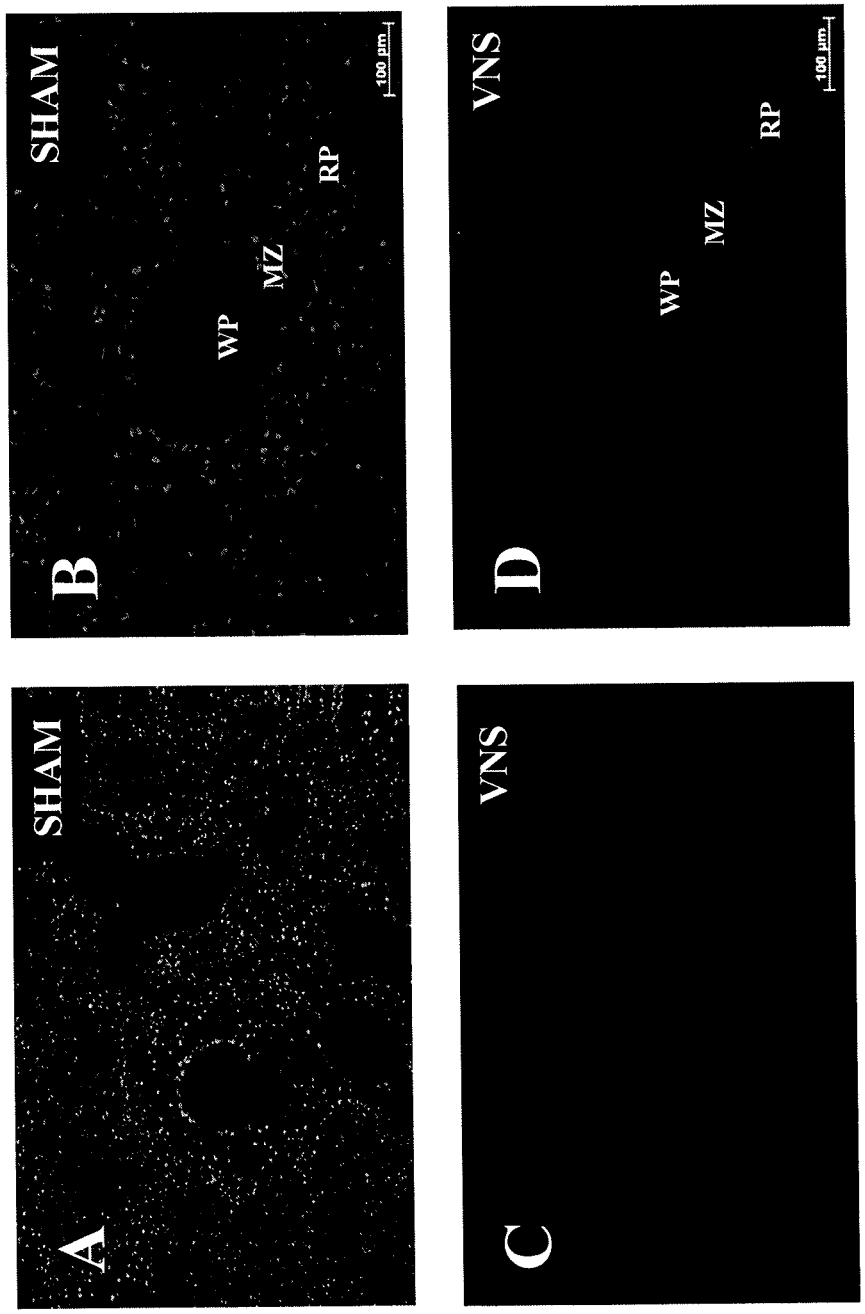
FIGS. 4A-4D are immunohistochemical staining of rats (through the spleen) after cutting the splenic nerve (FIGS. 4C and 4D) and in sham-operated rats, whose splenic nerve was left intact (FIGS. 4A and 4B); all rats were first subjected to vagus nerve stimulation and endotoxemia. Spleen sections were stained for TNF expression.

To study whether TNF-inhibiting signals in the vagus traverses the splenic nerve, the splenic nerve was surgically ablated in rats exposed to endotoxemia and vagus nerve stimulation. Splenic neurectomy prevented the TNF-suppressing activity of vagus nerve stimulation, indicating that the neural signals originating in the cervical vagus nerve traverse the splenic nerve (FIG. 1). Complete ablation of the splenic nerve was confirmed, because immunohistochemical staining for synaptophysin, a synaptic vesicle protein and marker of nerve terminals, was absent after the splenic nerve was cut (FIGS. 2A and 2B). Moreover, and as expected, review of sections stained using glyoxylic acid to reveal catecholaminergic neurons revealed that it was completely depleted in animals subjected to splenic neurectomy (FIGS. 2C and 2D). In agreement with previous studies, we observed synaptophysin-positive staining in the regions of the central artery, white pulp, red pulp, and splenic capsule. Sequential sections showed synaptophysin staining following a similar distribution pattern to that of the neural network visualized with glyoxylic acid.

To continue studying the functional and cellular anatomy of these nerves, it was necessary to characterize the cell source of spleen TNF during endotoxemia. Previous evidence suggested that the major source of TNF in endotoxemia is cells of the rethiculoendothelial system (Cano, G., A. F. Sved, L. Rinaman, B. S. Rabin, and J. P. Card. 2001. Characterization of the central nervous system innervation of the rat spleen using viral transneuronal tracing. *J. Comp Neurol.* 439:1-18.1), but the specific cell type was unknown. Accordingly, sections studied by immunohistochemistry revealed that TNF production occurred in the marginal zone and the red pulp regions, the areas where spleen macrophages reside. Immunohistochemistry with specific markers of macrophage subpopulations revealed the TNF-producing cells to be the marginal metallophilic macrophages, the marginal zone macrophages, and the red pulp macrophages (FIG. 3A-3D). We did not observe TNF-positive staining in either T lymphocytes or dendritic cells. These findings indicated that macrophages in the marginal zone and red pulp are the major source of spleen TNF in endotoxemia. In order to confirm the functional connection between vagus nerve signals and these TNF-producing macrophages, rats were subjected to vagus nerve stimulation and endotoxemia.

TNF expression in spleen was significantly abolished by vagus nerve stimulation (FIG. 4A-4D). Together these results indicate that signals originating in the vagus nerve attenuate TNF in spleen via the splenic nerve.

Figures 5A, 5B, 5C, 5D, 5E, 5F:
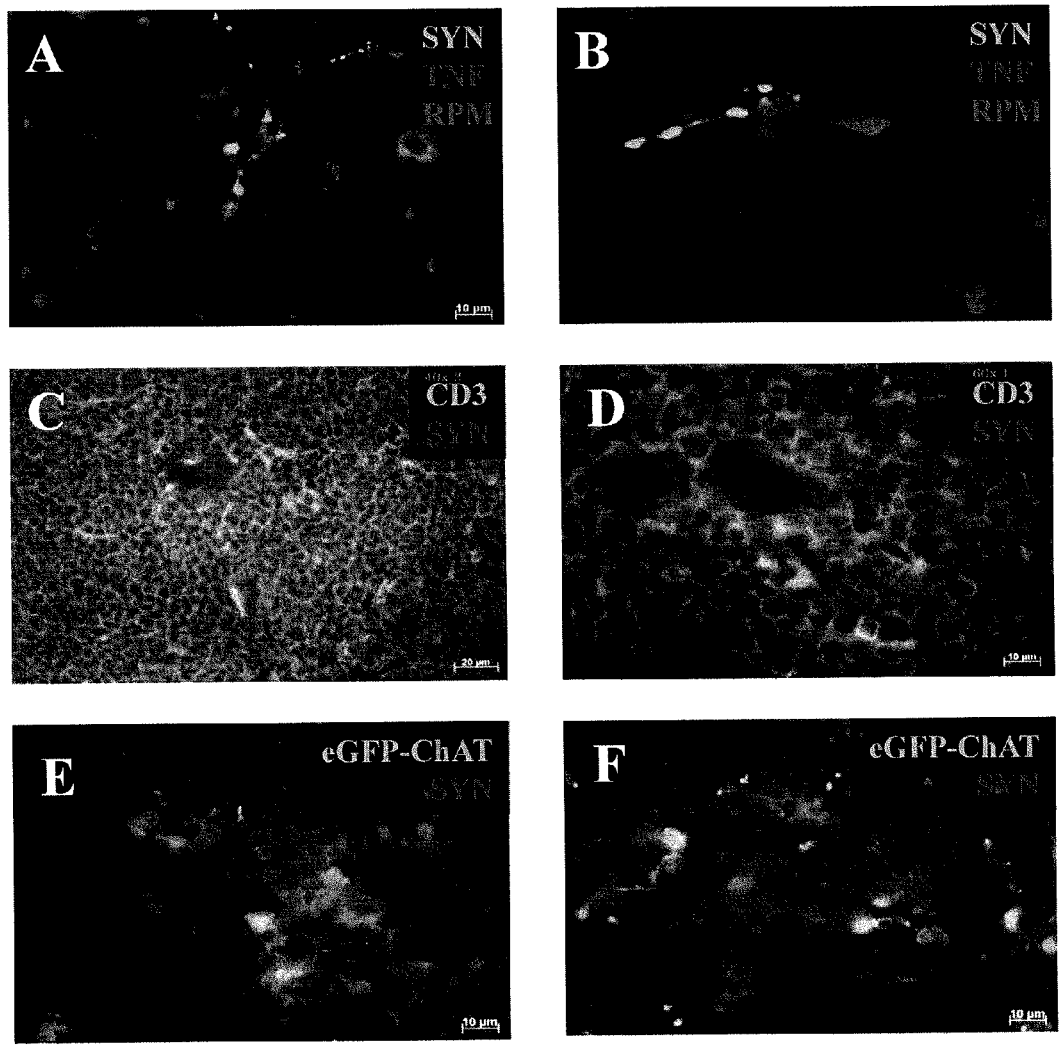
FIGS. 5A-5B show spleen sections stained for synaptophysin (SYN), TNF, and red pulp macrophages (RPM) in sham-operated (control) rats.
FIGS. 5C and 5D show spleen sections stained for synaptophysin (SYN) and CD3 (a T cell marker).
FIGS. 5E and 5F show spleen sections expressing eGFP placed under the control of endogenous ChAT transcriptional regulatory elements (eGFT-ChAT) and stained for synaptophysin (SYN).

We next undertook to understand the cellular basis for this control of cytokine production by specific nerves in discrete populations of macrophages. We performed a systematic search for points of contact between the splenic nerve endings and the TNF producing macrophages. Triple staining of spleen sections from sham-operated rats revealed nerve terminals adjacent to, and apparently contacting, the TNF-producing macrophages (FIGS. 5A and 5B). Nonetheless, these points of contact were difficult to visualize, and largely limited to the red pulp macrophages. Most important, not all of the TNF producing cells received neural input. Instead, it was clear that the major cells contacting the neurons were the T cell in the white pulp. Serial sections through white pulp areas revealed that synaptophysin-positive neurons provided abundant contact to T cells (FIGS. 5C and 5D). Previous investigators have shown that catecholaminergic neurons contact T cells in spleen, and that T cells express choline acetyltransferase, the enzyme required for acetylcholine production. BAC-transgenic mice, in which eGFP was placed under the control of endogenous ChAT transcriptional regulatory elements were used. Examination of eGFP-ChAT in spleen confirmed that T cells are the major source of acetylcholine synthesis in spleen. Moreover, nerve terminals made contact with some of these eGFP-ChAT-positive cells (FIGS. 5 E and 5F).

Figure 6A:
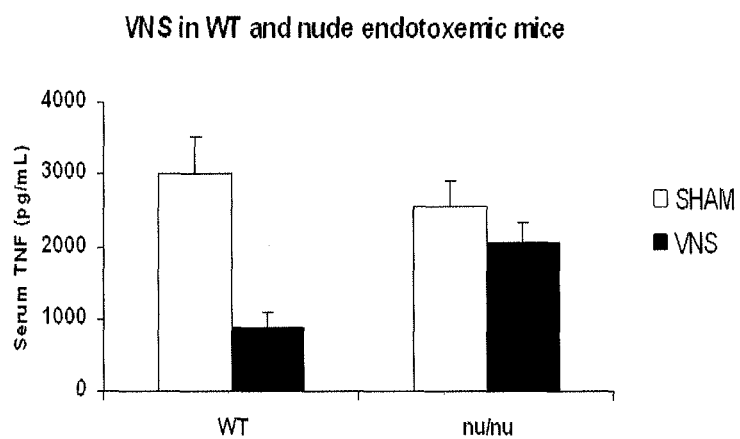
FIG. 6A shows the effect of serum TNF levels in wild-type (left) and nude (right) mice (mice devoid of T cells) after vagus nerve stimulation during endotoxemia. "SHAM" mice were not stimulated.
Figure 6B:
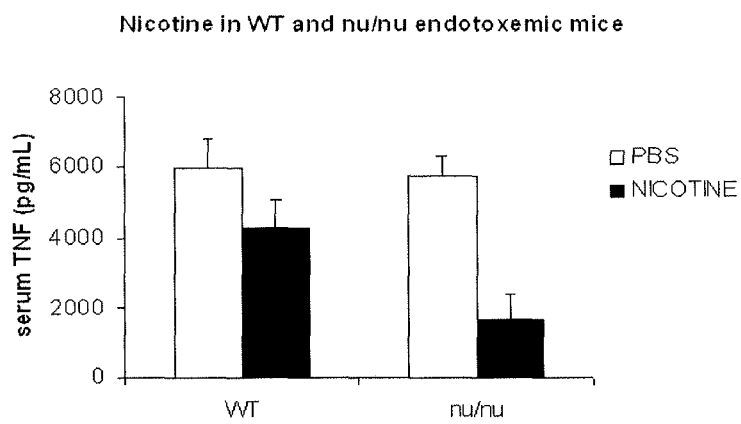
FIG. 6B shows the effect of serum TNF levels in wild-type (left) and nude (right) mice during endotoxemia after application of either saline (PBS) or nicotine.

Accordingly, we reasoned that the T cells might participate in the neural regulation of TNF in the spleen. Consistent with this, we discovered that vagus nerve stimulation of nude mice (mice devoid of T cells) failed to inhibit TNF production during endotoxemia (FIG. 6A). We (and others) have previously shown that the alpha7 nAChR is essential for the functional integrity of the cholinergic anti-inflammatory pathway. Administration of nicotine to nude mice significantly inhibited the production of TNF (FIG. 6B) indicating the absence of T cells does not impair the ability of the TNF producing macrophages to respond to the alpha7 nAChR agonist. Thus, we have shown the surprising result that T cells provide a critical role in transducing neural signals from the splenic nerve to the TNF-producing macrophages to control cytokine production via the cholinergic anti-inflammatory pathway.

These surprising results described herein expand our knowledge of the anatomical basis of the cholinergic anti-inflammatory pathway by showing that macrophage subpopulations in spleen produce TNF in endotoxemia, and that electrical stimulation of the vagus nerve controls TNF production by these cells via a mechanism that is dependent on an intact splenic nerve.

Previously, we found that vagus nerve stimulation attenuates spleen TNF, an effect that is dependent on the celiac branches of the vagus nerve. However, neuronal tracing studies and the lack of splenic cholinergic fibers indicate that primary vagus nerve fibers do not innervate the spleen. Our results show that suppression of TNF by vagus nerve stimulation requires an intact splenic nerve, a finding that indicates a functional connection between the vagus nerve and splenic TNF-producing cells. The spleen is innervated by nerve fibers that originate in the celiac ganglion. Efferent fibers of the vagus nerve, through its celiac branches, terminate in synaptic-like structures around principal cells of the celiac ganglion. Our data raise the possibility that an anti-inflammatory signal conveyed by the vagus nerve attains splenic immune cells through a system of two serially-connected neurons: one preganglionic that originates in the dorsal motor nucleus of the vagus embodied in the vagus nerve, and other postganglionic that originates in the celiac ganglion whose axons travel along the splenic nerve.

The splenic nerve, mainly composed of catecholaminergic fibers, is supplied by preganglionic sympathetic neurons located in the intermediolateral column of the thoracic spinal cord and the paravertebral ganglia (1). Our results indicate that the vagus nerve communicates with the splenic nerve. Vagal regulation of postganglionic catecholaminergic fibers has been demonstrated previously. In dogs, electrical stimulation of the cervical vagus nerve decreases pancreatic norepinephrine release induced by electrical stimulation of thoracic (catecholaminergic) nerves (2). In rats, cervical vagotomy increases splenic nerve discharge induced by IL-1β, suggesting that the vagus nerve exerts a tonic inhibitory control over splenic nerve activity (3). To our knowledge, preganglionic projections to postganglionic neurons in the celiac ganglion have not been characterized. For instance, it is unclear whether the splanchnic nerve (preganglionic sympathetic fiber) and the vagus innervate the same postganglionic neurons in the celiac ganglion.

Vagus nerve stimulation attenuates TNF mRNA and protein levels in spleens of endotoxemic animals but the target cell of this effect was unknown. Here we found that vagus nerve stimulation attenuated TNF in macrophages of the marginal zone and the red pulp. An earlier study using the perfused rat spleen ex vivo showed that electrical stimulation of the splenic nerve induces norepinephrine release from spleen, and attenuates LPS-induced TNF through a beta-adrenergic dependent mechanism (4). Given that electrical stimulation of the vagus nerve requires an intact splenic nerve in order to suppress TNF, it is plausible that vagus nerve stimulation induces release of norepinephrine from catecholaminergic splenic nerve terminals, whose presence has been previously revealed in the marginal zone and red pulp. Future experiments will aim to determine the effect of vagus nerve stimulation on the release of catecholamines and other neurotransmitters or neuropeptides (e.g. neuropeptide Y) in spleen.

One issue in the cholinergic anti-inflammatory pathway not addressed in this study is the anatomic location of the nicotinic acetylcholine receptor alpha7 subunit, which is required for vagus nerve control of TNF production. In vivo, we have observed that alpha7 knockout mice are insensitive to the TNF-suppressive effect of vagus nerve (5). In vitro, acetylcholine and other cholinergic agonists attenuate LPS-induced TNF in human and mouse macrophages, as well as in mouse splenocytes, through an alpha7-dependent mechanism (5,6). In view of the present findings it is possible that the alpha7 requirement observed in vivo is related to its functioning in autonomic ganglia, the alpha7 nicotinic subunit of the acetylcholine receptor is expressed in autonomic ganglia where it mediates fast synaptic transmission, and its expression has been documented in the superior cervical ganglion and the celiac ganglion (7,8). It is possible that acetylcholine released by the vagus nerve acts upon alpha7 expressed in neurons of the celiac ganglion to modulate splenic nerve function. Nevertheless, alpha7 involvement in cholinergic signaling in spleen, which contains and produces acetylcholine (9,10) and alpha7-expressing immune cells (11), has not been ruled out.

Here, we have found that several macrophage subpopulations are responsible for splenic TNF production in endotoxemia, and that their cytokine-producing capability is amenable to modulation by electrical stimulation of the vagus nerve, through a mechanism dependent on an intact splenic nerve. The spleen is a lymphoid organ where several leukocyte subtypes converge to initiate innate and adaptive immune responses, and splenic nerve endings are located in close proximity to macrophages and lymphocytes. Our finding that vagus nerve stimulation modulates splenic TNF production through the splenic nerve, suggest that vagus nerve stimulation could modulate adaptive immunity as well. Altogether, these findings extend our knowledge of the anatomical basis that allows control of cytokine production in the spleen by the vagus nerve.

Materials and Methods

Animals

Adult male BALB/c mice 8 to 12 weeks-old (20-25 g; Taconic) and adult male Sprague Dawley rats 8 to 12 weeks-old (250-300 g, Charles River Laboratories) were housed at 25° C. on a 12-hour light/dark cycle, and let acclimatize for one week before experiments were conducted. Water and regular rodent chow were available ad libitum. Experiments were performed under protocols approved by the Institutional Animal Care and Use Committee of the Feinstein Institute for Medical Research, North Shore-LIJ Health System.

Antibodies

Antibodies and dilutions used for immunofluorescence were as follows: Marginal zone macrophages: Biotinylated rat anti-mouse SIGN-R1 (clone ER-TR9, BMA Biomedicals); marginal metallophilic macrophages: Biotinylated rat anti-mouse sialoadhesin (clone MOMA-1, BMA Biomedicals); red pulp macrophages: Biotinylated rat anti-mouse F4/80 (clone A3-1, Serotec); neutrophils: Rat anti-mouse Gr-1 (clone RB6-8C5, R&D Systems); rat marginal zone macrophages: Mouse anti-rat CD169 (Clone ED3, Serotec); rat red pulp macrophages (Clone ED2, Serotec). Goat anti-mouse TNF (R&D Systems), and goat anti-rat TNF (R&D Systems). Secondary reagents: Cy3-conjugated Affinipure donkey anti-goat IgG (Jackson Immunoresearch Laboratories); FITC-conjugated Affinipure donkey anti-rabbit IgG (Jackson Immunoresearch Laboratories); Alexa Fluor 568-conjugated streptavidin (Molecular Probes); FITC-conjugated avidin (Molecular Probes).

Endotoxemia

Endotoxin (LPS from *E. coli*, 0111:B4, Sigma-Aldrich) was injected to animals (10 mg/kg, i.p. corresponding to a LD75 dose). Blood and spleens were harvested 10, 30, 60 or 120 minutes after LPS administration. We used ELISA to determine TNF concentration in serum (R&D Systems). Spleens were either snap frozen for further immunofluorescence analysis or disrupted in PBS plus protease inhibitor cocktail (Complete mini, Roche) with a tissue homogenizer (Polytron 3100, Kinematica). TNF content in spleen tissue was determined by ELISA and normalized to protein concentration (Protein Assay, BioRad). In some experiments, PBS or nicotine (Sigma-Aldrich) was injected 30 minutes (2 mg/kg, i.p.) prior to endotoxin administration. Animals were then euthanized 60 minutes later and spleens were harvested for TNF immunofluorescence or TNF quantification in tissue homogenates.

Electrical Stimulation of the Vagus Nerve

Male Sprague Dawley rats were anesthetized with urethane (4 g, i.p.) and xylazine (15 mg/kg, i.m.). Vagus nerve stimulation was performed as described previously (11). Briefly, a bipolar platinum electrode (Plastics One) was placed across the isolated cervical vagus nerve. Electrical stimulation (1V, 2 ms, 5 Hz) was generated by a stimulation module (STM100A) under the control of the AcqKnowledge software (Biopac Systems). Rats underwent 10 minutes of vagus nerve stimulation before and after endotoxin injection. In rats subjected to sham surgery, the vagus nerve was only exposed.

Immunofluorescence

All samples were fresh-frozen with dry ice, embedded in O.C.T, compound (Tissue-Tek) and kept at −20° C. until processing. Ten µm-thick spleen slices were cut using a cryostat and mounted on glass slides and air-dried for five minutes. The tissue was then permeabilized with PBS-saponin 0.1% for 30 minutes. All incubation periods were performed at room temperature in a humid chamber. The primary antibodies were diluted in PBS-saponin 0.1% at the following concentrations: TNF (1:6 dilution), MOMA-1 (1:1000 dilution), ER-TR9 (1:100 dilution), F4/80 (1:50). After a 2-hour incubation period, the slides were washed 3 times in washing buffer (PBS, tween 20 0.02%), incubated with avidin-FITC and Cy3-labeled rat anti-goat IgG, both diluted 1:250 in PBS-saponin 0.1% for 30 minutes. Finally, the slides were washed, dried, mounted (Vectashield) and observed through a Zeiss Axiovert 20 inverted microscope. Images were analyzed using the AxioVision V5 software (Carl Zeiss).

Methods of Treatment

In general, an inflammatory response may be treated based on this new discovery. In particular, an inflammatory reflex may be treated by stimulating a subject's inflammatory reflex to inhibit the immune response, and administering a T-cell modifying agent.

The inflammatory reflex may include the vagus nerve, the splenic nerve, the hepatic nerve and the trigeminal nerve, and their afferents and efferents. For example, Tracey et. al., have previously reported that the nervous system regulates systemic inflammation through a vagus nerve pathway. This pathway may involve the regulation of inflammatory cytokines and/or activation of granulocytes. Thus, it is believed that appropriate modulation of the vagus nerve may help regulate inflammation. In some variations the inflammatory reflex may be limited to one or more of these nerves (or its afferents or efferents), such as the vagus nerve.

The inflammatory reflex may be stimulated by any appropriate method, particularly electrical or mechanical stimulation. Other forms of stimulation include magnetic stimulation, thermal stimulation, etc. When electric and mechanical stimulation is used, this stimulation may be performed without desensitizing the inflammatory reflex. For example, the stimulation may be performed by an electrode or actuator that does not directly contact the nerve. Any appropriate stimulation may be used, particularly stimulation which results in a long-lasting (and repeatable) inhibition of inflammation, including cytokine levels. Examples of such stimulation are provided in the documents incorporated by reference, but may include stimulation at extremely low duty-cycle such as stimulation for less than 5 minutes once every 6 hours, every 12 hours, every 24 hours, or longer. An exemplary electrical stimulation may be stimulation at in the range of 10 mV to 5 V at a frequency of 0.1 Hz to 100 Hz, with a duration of stimulation between from 1 ms to 10 min.

In some variations, the stimulation is modified by the addition of the T-cell modification agent. For example, stimulation may be reduced in intensity (e.g., voltage, pressure, etc.) or in duration (e.g., frequency within stimulation pulse) or in regularity (e.g., duration between stimulation pulses), or the like. Feedback (open loop or closed loop) may be used to set the intensity, duration, and/or regularity of stimulation.

The stimulation of the inflammatory pathway may be provided by an external device, an internal (e.g., implanted) device, or a device having both internal and external components. For example, a stimulation device may include a non-contact electrode that does not contact a nerve of the inflammatory reflex, an energy source to apply energy to the electrode(s) and a controller. The controller may control the application of energy to the electrode(s). For example, the controller may initially cause the stimulator to apply stimulation once or twice a day for 1 minute of 0.1 V stimulation having a frequency of 1 Hz and a duration of 50 ms. The stimulator may be part of a system for treating the inflammatory reflex, which may also include one or more sensors, including feedback sensors. Feedback sensors may help control the system, including the application of stimulation to the inflammatory pathway, and/or the administration of one or more T-cell modulating agents.

Agents that modulate T-cells may include immunosuppressants and immunomodulators. For example, agents such as glucocorticoids (e.g., dexamethasone, hydrocortisone, prednisone, prednisolone, etc.), antibody agents (e.g., antibodies or fragments directed against the CD3 molecule of the T-cell antigen receptor complex, such as Muromonab CD3(OKT-3), etc.), peptide agents (e.g., immunosuppressive agents including Cyclosporine, etc.). Drugs (e.g., tacrolimus, Aspirin-like drugs (ALD), etc.) and "pro-drugs" (such as Azathioprine, Mycophenolate Mofetil, Methotrexate, etc.) are also included. Agents may act directly on T-cells or indirectly to affect T-cells. For example, agents may interact with receptors on the surface of the T-cell (e.g., caspase 8 inhibitor c-FLIP(L), and related agents), and may modulate (e.g., inhibit or enhance) T-cell response and/or proliferation. The examples provided above are not exhaustive, and any agent which may be used to modulate T-cells (e.g., T-cell activity or proliferation) may be used.

The modulation of T-cells may include potentiating activity, including potentiating acetylcholine (ACh) activity. For example, a T-cell modifying agent may include an agent that potentiates release of acetylcholine. Such agents may include small molecules, antibodies, peptides, or the like. For example, anti-CD11a antibodies have been shown in some circumstances to enhance or trigger release of acetylcholine (e.g., T. Fujii, K. Masuyama, K. Kawashima, "Simvastatin regulates non-neuronal cholinergic activity in T lymphocytes via CD11a-mediated pathways" J Neuroimmunol. 2006 October; 179(1-2):101-7. Epub 2006 Jul. 10). In some variations, the T-cell modifying agent may potentiate the stability of ACh, for example, by preventing uptake and/or breakdown of ACh. For example, the activity of the T-cell may be modulated by inhibiting acetylcholine esterase. Alternatively, the activity of the T-cell may be modulated by destabilizing (e.g., removing) acetylcholine; for example, by adding esterase.

In general, the methods and systems described herein are directed to the treatment of inflammation by modulating T-Cell activity, in some variations the activity of acetylcholine is directly modulated, so that sources of acetylcholine or agonists and antagonists implicated in the acetylcholine signaling pathway (e.g., acetylcholine receptors, etc.) including non-T-cell sources may also be manipulated as part of the methods and systems described herein. For example, the method may include a method of coordinating stimulation of the subject's inflammatory reflex to inhibit the inflammatory response and administering an agent that modulates or potentiates splenic acetylcholine, which may include acetylcholine released by T-cells.

Agents or drugs may be delivered systemically to the subject, or they may be delivered locally. For example, agents may be delivered orally, intraveneously, intramuscularly, etc. In some variations, the agent may be delivered by an implant. For example, the implant may be part of a system for stimulating (e.g., electrically, mechanically, etc.) the inflammatory reflex. In some variations the T-cell modifying agent is applied locally to the spleen, including the region communicating with the spleen (e.g., splenic region).

The method of treating an inflammatory response may be used to treat any inflammatory response, including an inflammatory disorder. Any inflammatory disorder may be treated in this manner. For example, disorders mediated by a cytokine response may be treated as described herein.

Examples of inflammatory disorders may include (but are not limited to): transplant rejection, rheumatoid arthritis, Psoriasis, or multiple sclerosis. Inflammatory disease that include T-cell mediated diseases may include: inflammatory bowel disease, systemic lupus erythematosis, rheumatoid arthritis, juvenile chronic arthritis, spondyloarthropathies, systemic sclerosis (scleroderma), idiopathic inflammatory myopathies (dermatomyositis, polymyositis), Sjogren's syndrome, systemic vaculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic polyneuropathy, hepatobiliary diseases such as infectious hepatitis (hepatitis A, B, C, D, E and other nonhepatotropic viruses), autoimmune chronic active hepatitis, primary biliary cirrhosis, granulomatous hepatitis, and sclerosing cholangitis, inflammatory and fibrotic lung diseases (e.g., cystic fibrosis), gluten-sensitive enteropathy, Whipple's disease, autoimmune or immune-mediated skin diseases including bullous skin diseases, erythema multiforme and contact dermatitis, psoriasis, allergic diseases of the lung such as eosinophilic pneumonia, idiopathic pulmonary fibrosis and hypersensitivity pneumonitis, transplantation associated diseases including graft rejection and graft-versus host disease, Psoriasis and other skin disorders.

The step of administering a T-cell modifying agent may be performed at any point in the methods described herein, as appropriate. For example, in some variations, the T-cell modifying agent is administered concurrent with the stimulation of the inflammatory reflex. In some variations the T-cell modifying agent is given before stimulation of the inflammatory reflex (e.g., seconds, minutes, hours, or days before). In some variations, the T-cell modifying agent is given after stimulation of the inflammatory reflex (e.g., seconds, minutes, hours, or days after). Multiple administrations of T-cell modifying agents may be given. In some variations, multiple T-cell modifying agents may be given either simultaneously or at different times.

The benefit of both administration of T-cell modifying agents and stimulation of the inflammatory reflex may result in an enhanced effect that would otherwise be seen with either stimulation or administration alone. This may allow a decreased amount of stimulation or administration to be provided. In some instances the effect may be further enhanced by the combination. For example, a T-cell modifying agent that does not significantly inhibit inflammation may be effective to inhibit an inflammatory response when combined with stimulation of the vagus nerve or some other component of the inflammatory reflex.

In some variations, an agent that modifies T-cell activity may be applied to inhibit the inflammatory reflex, which may otherwise be stimulated. For example, an agent that inhibits T-cell activity (and/or proliferation) may be provided to inhibit the inflammatory reflex, which may enhance inflammation, or may remove an inhibition on inflammation.

A method of treating a T cell-mediated diseases may include the steps of identifying a patient suffering from a condition mediated by T-cell cells, stimulating the subject's inflammatory reflex, and administering a T-cell modifying agent.

A "T-cell mediated" disease means a disease in which T cells directly or indirectly mediate or otherwise contribute to the morbidity in a mammal. The T cell mediated disease by be associated with cell mediated effects, lymphokine mediated effects, etc. and even effects associated with B cells if the B cells are stimulated, for example, by the lymphokines secreted by T cells.

Figure 7A:
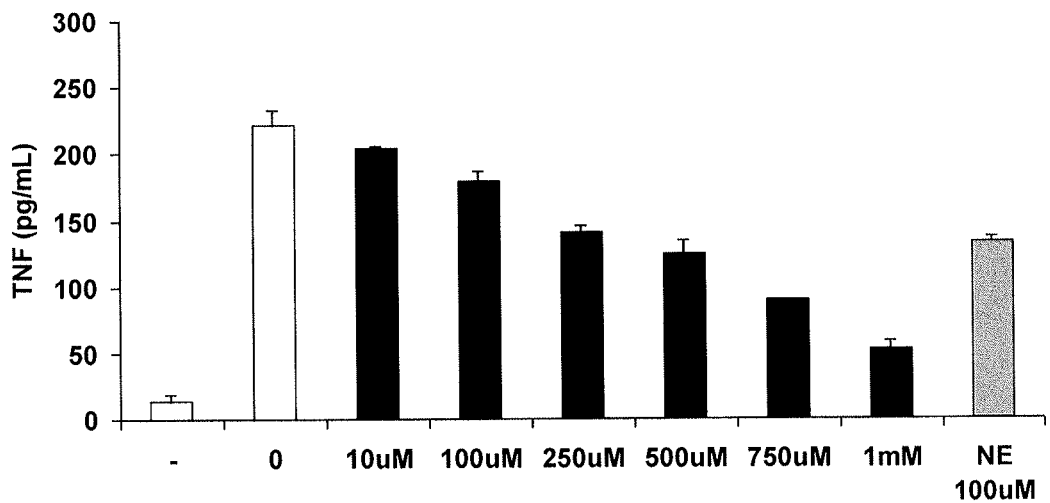
FIG. 7A shows the effect of a cholinesterase inhibitor, Paraoxon, on TNF production by LPS-stimulated spleen cells, indicating a dose-dependent inhibition of TNF.
Figure 7B:
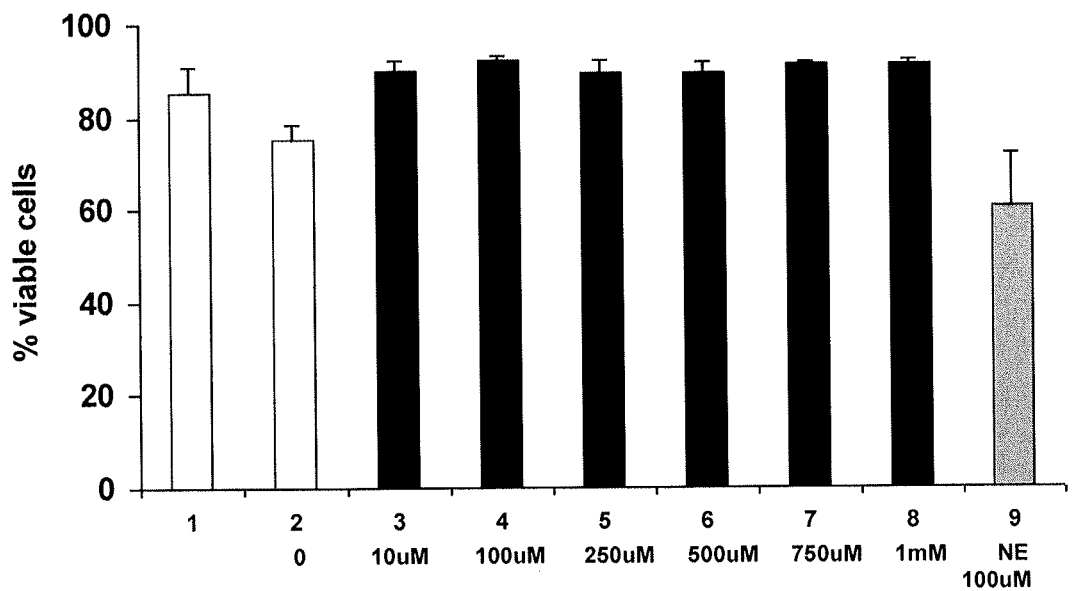
FIG. 7B indicates that here is no significant toxicity correlated to these levels of Paraoxon.

Compounds that modify the Acetylcholine response of the T-cells are one class of T-cell modifying agents that may be used herein. For example, a T-cell modifying agent may include a material that effects either the release, the update, or the breakdown of acetylcholine in the spleen, and particularly by the T-cells in proximity to the splenic nerve endings. For example, FIGS. 7A and 7B illustrates the effect of Paraoxon on spleen cells. Paraoxon is a cholinesterase inhibitor. FIG. 7A shows that increasing the amount of AChE inhibitor in whole spleen cell cultures stimulated with LPS results in a blunted TNF response. As mentioned above, the source of TNF in LPS-stimulated spleen cell cultures is thought to be the splenic macrophage population. Based on the data provided herein (e.g., FIG. 7A), there is an endogenous source of acetylcholine in the whole spleen cell preparation, and if the activity of ACh is increased in these cultures by inhibiting AChE, the TNF response is effectively blunted.

Although the spleen is innervated by catecholaminergic nerve fibers, neural cholinergic input is absent. However, the spleen contains acetylcholine and releases it upon electrical stimulation of the splenic nerve. In order to characterize the source of acetylcholine in spleen, we used transgenic mice in which enhanced green fluorescent protein (eGFP) is expressed under control of transcriptional regulatory elements of choline acetyltransferase, the enzyme that synthesizes acetylcholine. eGFP was detected in spleen B and T cells, some of which were located in close proximity to nerve endings in the parenchyma of the white pulp. Paraoxon, a cholinesterase inhibitor that enhances cholinergic transmission by preventing hydrolysis of acetylcholine, dose-dependently attenuated TNF levels in spleen cell suspensions stimulated with LPS without affecting cell viability, suggesting that acetylcholine derived from lymphocytes is involved in regulation of spleen TNF.

For example, FIG. 7A illustrates the effect of increasing concentrations of Paraoxon on TNF production by LPS-stimulated spleen cells of BALB/c 18 week old mice. As mentioned above, as the amount of Paraoxon is increased (thereby increasing the amount of acetylcholine by increasing the inhibition of AChE), the greater the inhibition of TNF. In this example, differing concentrations of Paraoxon were included in various individual wells (having $5\times10^6$ cell/well) with a total volume of 250 microliters/well, and stimulated for 4 hours with LPS (500 ng/mL). FIG. 7B illustrates that for the concentrations of Paraoxon used in FIG. 7A, there was no significant loss of viability, so the effect was not likely due to a reduction in macrophages or other cells producing TNF, but is instead the result of inhibition of TNF production due to acetylcholine.

Thus, inflammation may be inhibited by stimulating the inflammatory reflex and by administering a T-cell modifying agent, as mentioned above. In some variations, the inflammatory response may be inhibited by stimulating a subject's inflammatory reflex and administering a T-cell modifying agent that enhances the ACh component of the inflammatory reflex (either before, during, or after stimulation of the inflammatory reflex).

In some variations a system for modulating an inflammatory response by modifying a subject's T-cells includes one or more components for stimulating a portion of the inflammatory reflex (e.g., the vagus nerve), and one or more components for applying a T-cell modifying agent. The component for stimulating the T-cell modifying agent may be an implant that releases one or more compounds that modify the activity of a T-cell. For example, the system may include an implantable drug delivery system that releases a compound. The implantable drug delivery system may be configured to be implanted in or near the spleen, so that the drug may be delivered to the spleen, and particularly near the terminals of the splenic nerve adjacent to T-cells and/or macrophages. In general the component for applying a T-cell modifying agent (e.g., a drug-delivery system or sub-system) and the component for stimulating a portion of the inflammatory reflex (e.g., a vagus nerve stimulator) communicate so that the stimulation of the inflammatory reflex may be coordinated with the modification of the T-cells. Thus, the system may be configured so that the T-cell modifying agent is applied either before or during (or in some cases, after) the stimulation of one or more portion of the inflammatory reflex.

Figure 8A:
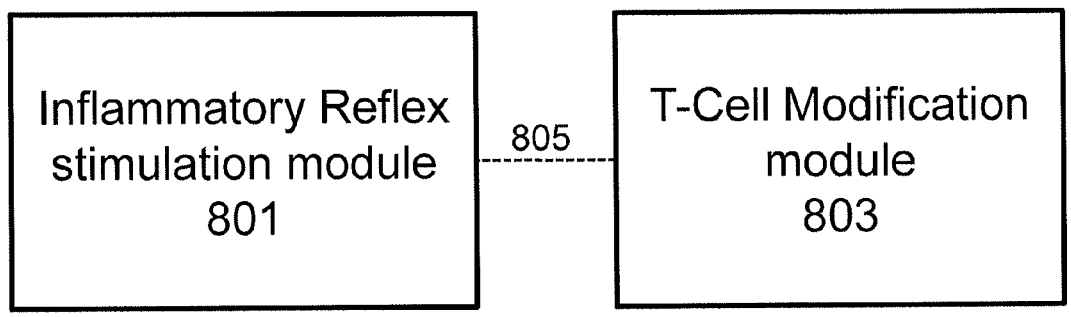
FIG. 8A illustrates a schematic of a general system for modulating an inflammatory reflex.
Figure 8B:
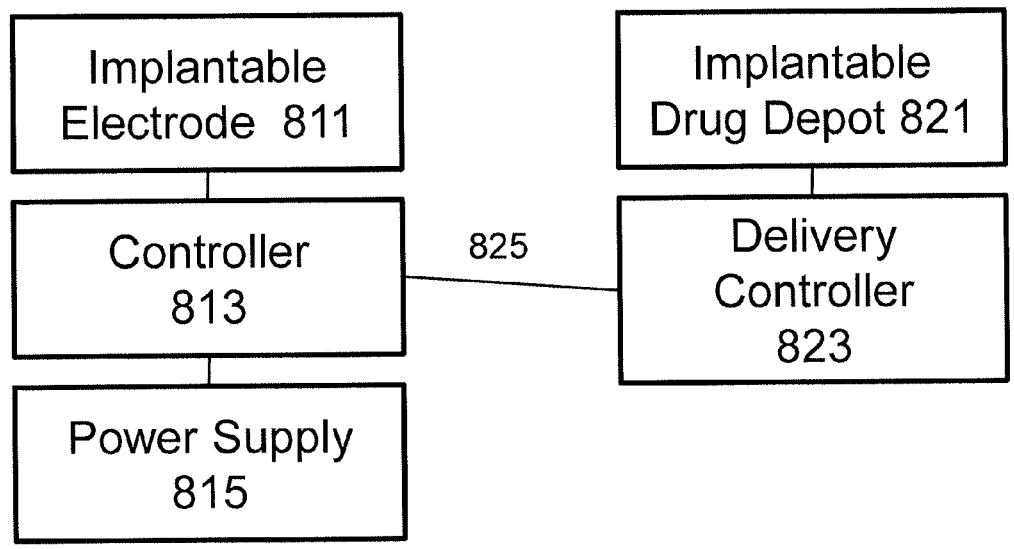
FIG. 8B is a schematic illustration of one variation of system for modulating an inflammatory reflex.

FIG. 8A illustrates a schematic of one variation of a general system for modulating an inflammatory reflex, as described herein, including an inflammatory reflex stimulation module 801 and a T-cell modification module 803. These two modules may communicate (e.g., wirelessly or via direct connection 805). In some variations, the system includes a controller for coordinating the activity of these modules. FIG. 8B is a schematic illustration of one variation of this system. In FIG. 8B, the inflammatory reflex stimulation module includes an implantable electrode for stimulating the vagus nerve 811, a controller for coordinating the stimulation from the electrode 813, and a power supply 815 for providing the power (e.g., battery). The power supply and/or controller may be implantable with the electrode, or they may be external. The T-cell modification module includes an implantable drug depot 821, and a delivery controller 823 for controlling the release of drug from the implantable drug depot 823. The drug depot is configured to be implanted (e.g., in or near the spleen) and to deliver drugs to reach the T-cells (or a subpopulation of the T-cells) in the spleen and modify their activity. Any of the agents mentioned herein for modifying the T-cell response may be used. The drug depot may be powered or passive. The delivery controller for the drug depot may communicate directly or indirectly (e.g., wirelessly) 825 with the controller for the vagus nerve stimulator. Any of these systems may include a controller for coordinating the stimulation between the inflammatory reflex stimulation module and the T-cell modifying agent module.

In some embodiments, the drugs delivered in conjunction with vagus nerve stimulation include anti-inflammatory drugs such as TNF blockers or IL-6 inhibitors. This treatment may combine two independent therapies for treating inflammation. Other drugs include drugs which suppress immune function by blocking one or more immune mediators, or immune cell function, or alternatively, target an immune cell for destruction, thereby suppressing immune function. The drugs may be administered as described herein. For example, the drugs may be injected into the patient's blood or muscle or under the skin. Alternatively, the drugs can be delivered using a drug depot or other implantable drug delivery device. In some embodiments, the drugs can be encapsulated in an extended release formulation to provide long term release of the drug. Table 2 below provides examples of these drugs, the immune mediator or cell that is inhibited by these drugs, and the indications in which these drugs are used.

TABLE 2

| Immune mediator or cell inhibited | Examples of drugs | Indications |
|---|---|---|
| TNF | etanercept, adalimumab, infliximab, golimumab, certolizumab pegol | Crohn's, psoriasis, rheumatoid arthritis, ankylosing spondylitis, psoriatic arthritis |
| IL-6 or IL-6 receptor | tocilizumab | Rheumatoid arthritis |
| T cell-antigen presenting cell interaction | abatacept | Rheumatoid arthritis |
| Janus-Activated Kinase (JAK) | tofacitinib | Rheumatoid arthritis |
| Spleen-Associated Kinase (SyK) | fostamatinib | investigational |
| B-cell (CD20) | rituximab | Rheumatoid arthritis |
| IL-1 | anakinra | Rheumatoid arthritis, CAPS syndrome |
| B-cell (BAFF/BLySS)) | belimumab | Systemic lupus erythematosus |
| T cell (CD25/IL-2R) | daclizumab | Multiple sclerosis |
| α4-integrin (cell adhesion) | natalizumab | Multiple sclerosis |
| T, B, NK cell lysis (CD52) | alemtuzumab | Multiple sclerosis |
| sphingosine-1-phosphate receptor modulator, sequesters lymphocytes in lymph nodes | fingolimod | Multiple sclerosis |
| Nuclear factor (erythroid-derived 2)-like 2 (Nrf2) pathway activator | dimethyl fumarate (DMF) | Multiple sclerosis |
| $\alpha_4\beta_7$ integrin (cell adhesion) | vedolizumab | Crohn's |
| IL-23 | ustekinumab | psoriasis |
| IL-17 | brodalumab and ixekizumab | Rheumatoid arthritis, psoriasis |

While the devices, systems, and methods of using them have been described in some detail here by way of illustration and example, such illustration and example is for purposes of clarity of understanding only. It will be readily apparent to those of ordinary skill in the art in light of the teachings herein that certain changes and modifications may be made thereto without departing from the spirit and scope of the invention.

REFERENCES

1. Cano, G., A. F. Sved, L. Rinaman, B. S. Rabin, and J. P. Card. 2001. Characterization of the central nervous system innervation of the rat spleen using viral transneuronal tracing. *J. Comp Neurol.* 439:1-18.
2. Benthem, L., T. O. Mundinger, and G. J. Taborsky, Jr. 2001. Parasympathetic inhibition of sympathetic neural activity to the pancreas. *Am. J. Physiol Endocrinol. Metab* 280:E378-E381.
3. Saindon, C. S., F. Blecha, T. I. Musch, D. A. Morgan, R. J. Fels, and M. J. Kenney. 2001. Effect of cervical vagotomy on sympathetic nerve responses to peripheral interleukin-1beta. *Auton. Neurosci.* 87:243-248.
4. Kees, M. G., G. Pongratz, F. Kees, J. Scholmerich, and R. H. Straub. 2003. Via beta-adrenoceptors, stimulation of extrasplenic sympathetic nerve fibers inhibits lipopolysaccharide-induced TNF secretion in perfused rat spleen. *J. Neuroimmunol.* 145:77-85.
5. Wang, H., M. Yu, M. Ochani, C. A. Amelia, M. Tanovic, S. Susarla, J. H. Li, H. Wang, H. Yang, L. Ulloa, Y. Al-Abed, C. J. Czura, and K. J. Tracey. 2003. Nicotinic acetylcholine receptor alpha7 subunit is an essential regulator of inflammation. *Nature* 421:384-388.
6. Borovikova, L. V., S. Ivanova, M. Zhang, H. Yang, G. I. Botchkina, L. R. Watkins, H. Wang, N. Abumrad, J. W. Eaton, and K. J. Tracey. 2000. Vagus nerve stimulation attenuates the systemic inflammatory response to endotoxin. *Nature* 405:458-462.
7. Del Signore, A., C. Gotti, A. Rizzo, M. Moretti, and P. Paggi. 2004. Nicotinic acetylcholine receptor subtypes in the rat sympathetic ganglion: pharmacological characterization, subcellular distribution and effect of pre- and postganglionic nerve crush. *J. Neuropathol. Exp. Neurol.* 63:138-150.
8. Lips, K. S., P. Konig, K. Schatzle, U. Pfeil, G. Krasteva, M. Spies, R. V. Haberberger, S. A. Grando, and W. Kummer. 2006. Coexpression and spatial association of nicotinic acetylcholine receptor subunits alpha7 and alpha 10 in rat sympathetic neurons. *J. Mol. Neurosci.* 30:15-16.
9. Bulloch, K., T. Damavandy, and M. Badamchian. 1994. Characterization of choline O-acetyltransferase (ChAT) in the BALB/C mouse spleen. *Int. J. Neurosci.* 76:141-149.
10. Rinner, I., K. Kawashima, and K. Schauenstein. 1998. Rat lymphocytes produce and secrete acetylcholine in dependence of differentiation and activation. *J. Neuroimmunol.* 81:31-37.
11. Huston, J. M., M. Ochani, M. Rosas-Ballina, H. Liao, K. Ochani, V. A. Pavlov, M. Gallowitsch-Puerta, M. Ashok, C. J. Czura, B. Foxwell, K. J. Tracey, and L. Ulloa. 2006. Splenectomy inactivates the cholinergic antiinflammatory pathway during lethal endotoxemia and polymicrobial sepsis. *J. Exp. Med.* 203:1623-1628.

What is claimed is:

1. A method of treating an inflammatory response, the method comprising:
stimulating a subject's inflammatory reflex to inhibit the inflammatory response by stimulating the subject's vagus nerve, wherein the stimulation is selected from the group consisting of electrical stimulation of the vagus nerve and mechanical stimulation of the vagus nerve, wherein the step of stimulating the subject's inflammatory reflex is repeated at regular intervals of at least about 4 hours; and
administering an anti-inflammatory drug.

2. The method of claim 1, wherein the step of stimulating the subject's inflammatory reflex comprises electrically stimulating the subject's inflammatory reflex to inhibit the immune response.

3. The method of claim 1, wherein the step of administering the anti-inflammatory drug comprises systemic administration of the anti-inflammatory drug.

4. The method of claim 1, wherein the step of administering the anti-inflammatory drug comprises administering the anti-inflammatory drug before stimulating the inflammatory reflex.

5. The method of claim 1, wherein the step of stimulating the inflammatory reflex comprises repeatedly and periodically stimulating the subject's inflammatory reflex.

6. The method of claim 1, wherein the anti-inflammatory drug is a TNF blocker or an IL-6 inhibitor.

7. The method of claim 1, wherein the inflammatory response is due to rheumatoid arthritis, psoriasis, multiple sclerosis, or Crohn's disease.

8. A method of treating an inflammatory response, the method comprising:
  stimulating a subject's inflammatory reflex to inhibit the inflammatory response by stimulating the subject's vagus nerve, wherein the stimulation is selected from the group consisting of electrical stimulation of the vagus nerve and mechanical stimulation of the vagus nerve, wherein the step of stimulating the subject's inflammatory reflex is repeated at regular intervals of at least about 4 hours; and
  administering a drug that suppresses immune function by blocking one or more immune mediators, wherein the immune mediator is selected from the group consisting of TNF, IL-6, IL-6 receptor, janus-activated kinase, spleen-associated kinase, CD20, B-cell activating factor, B lymphocyte stimulator, CD25, IL-2R, IL-1, α4-integin, CD52, sphingosine-1-phosphate receptor modulator, nuclear factor (erythroid-derived 2)-like 2 pathway activator, $\alpha_4\beta_7$ integrin, IL-23, and IL-17.

9. The method of claim 8, wherein the step of stimulating the subject's inflammatory reflex comprises electrically stimulating the subject's inflammatory reflex to inhibit the immune response.

10. The method of claim 8, wherein the step of administering the drug comprises systemic administration of the drug.

11. The method of claim 8, wherein the inflammatory response is due to rheumatoid arthritis, psoriasis, multiple sclerosis, or Crohn's disease.

\* \* \* \* \*